(12) United States Patent
Higazi et al.

(10) Patent No.: US 9,072,737 B2
(45) Date of Patent: Jul. 7, 2015

(54) TPA MUTANT IN THE TREATMENT OF ACUTE BRAIN INJURY AND NEURODEGENERATIVE DISORDERS

(75) Inventors: Abd Higazi, D.N. Shimshon (IL); Nuha Hijazi, D.N. Shimshon (IL)

(73) Assignee: HADASIT MEDICAL RESEARCH SERVICES & DEVELOPMENT LTD., Jerusalem (IL)

( * ) Notice: Subject to any disclaimer, the term of this patent is extended or adjusted under 35 U.S.C. 154(b) by 228 days.

(21) Appl. No.: 12/922,551

(22) PCT Filed: Mar. 16, 2009

(86) PCT No.: PCT/IL2009/000300
§ 371 (c)(1),
(2), (4) Date: Sep. 14, 2010

(87) PCT Pub. No.: WO2009/116035
PCT Pub. Date: Sep. 24, 2009

(65) Prior Publication Data
US 2011/0008313 A1    Jan. 13, 2011

(30) Foreign Application Priority Data
Mar. 16, 2008   (IL) .......................................... 190184

(51) Int. Cl.
| | | |
|---|---|---|
| *A61K 38/49* | (2006.01) | |
| *A61K 38/26* | (2006.01) | |
| *A61K 38/28* | (2006.01) | |
| *A61K 38/45* | (2006.01) | |
| *C12N 9/72* | (2006.01) | |

(52) U.S. Cl.
CPC ................ *A61K 38/49* (2013.01); *A61K 38/26* (2013.01); *A61K 38/28* (2013.01); *A61K 38/45* (2013.01); *C12N 9/6459* (2013.01); *C12Y 304/21069* (2013.01)

(58) Field of Classification Search
None
See application file for complete search history.

(56) References Cited

U.S. PATENT DOCUMENTS

2004/0071707 A1 * 4/2004 Carroll et al. .............. 424/146.1

FOREIGN PATENT DOCUMENTS

| WO | 00/32759 | 6/2000 |
| WO | 00/32759 A1 | 6/2000 |
| WO | 02/40650 | 5/2002 |
| WO | 2005/026341 | 3/2005 |

OTHER PUBLICATIONS

Campana et al, The low-density lipoprotein receptor-related protein is a pro-survival receptor in Schwann cells: possible implications in peripheral nerve injury. J Neurosci. Oct. 25, 2006;26(43):11197-207.*
Parathath et al, Nitric oxide mediates neurodegeneration and breakdown of the blood-brain barrier in tPA-dependent excitotoxic injury in mice. J Cell Sci. Jan. 15, 2006;119(Pt 2):339-49.*
Bu et al, Cellular receptors for the plasminogen activators. Blood. Jun. 15, 1994;83(12):3427-36.*
Kilic et al, The phosphatidylinositol-3 kinase/Akt pathway mediates VEGF's neuroprotective activity and induces blood brain barrier permeability after focal cerebral ischemia. FASEB J. Jun. 2006;20(8):1185-7. Epub Apr. 26, 2006.*
Mori et al, Reduced cortical injury and edema in tissue plasminogen activator knockout mice after brain trauma. Neuroreport. Dec. 21, 2001;12(18):4117-20.*
Arundine et al, Molecular mechanisms of glutamate-dependent neurodegeneration in ischemia and traumatic brain injury. Cell. Mol. Life Sci. 61 (2004) 657-668.*
Gravais et al, Tissue-type plasminogen activator as a therapeutic target in stroke. Expert Opin. Ther. Targets (2008) 12(2) p. 159-170.*
Goodnight, S.H. et al. N. Engl. J. Med. 290:1043-1047 (1974).
Stein, S.C. et al. J. Neurosurg.97:1373-1377 (2002).
Stein, S.C. et al. Neurosurgery 32:25-30; discussion 30-21(1993).
Carmeliet, P. et al. Nature, 369:419-424 (1994).
Bdeir, K. et al. Blood, 96:1820-1826 (2000).
Abe, Y. et al. Journal of Neurotrauma, 20:43-57 (2003).
Wang, Y. et al. Nat Med, 4:228-231 (1998).
Tabrizi, P. et al. Arterioscler. Thromb. Vasc. Biol., 19:2801-2806 (1999).
Nassar, T. et al. Blood, 103:897-902 (2004).
Faraci, F.B., KR. Circulation Research. 1993,72:476-480 (1993).
Choi, D. Journal of Neurobiology, 23:1261-1276 (1992).
Katayama Y, B.D. et al. Journal of Neurosurgery, 73:889-900 (1990).
Kawamata, T.K. et al. Journal of Cerebral Blood Flow and Metabolism, 12:12-24 (1992).
Nicole O, D.F. et al. Nat. Med., 7:59-64 (2001).
Yepes et al. J. Clin. Invest. 112:1533-1540 (2003).
LaPlaca MC and Thibault LE, J. Neurosci. Res. Apr. 15, 1998;52(2):220-9.
Chen, Y., Constantini, S., Trembovler, V., Weinstock, M. & Shohami, E. (1996) J. Neurotrauma 13, 557-568.
Beni-Adani, L. J. Pharmacol. Exp. Ther. 296:57-63 (2001).
Zlotnik, A. et al. Exp. Neurology 203:213-220 (2007).
Gottlieb, M. J. Neurochem. 87:119-126 (2003).
Kunitada S et al: "Inhibition of clot lysis . . . retraction." Blood Mar. 15, 1992, vol. 79, No. 6, Mar. 15, 1992, pp. 1420-1427, XP002538295.
Database Genbank NCBI; Oct. 18, 2006, Venter, J.C. et al, "plasminogen activator, tissue, isoform CRA__ [Homosapiens]" XP002538297, Database access No. EAW63231.

(Continued)

*Primary Examiner* — Sheridan Swope
(74) *Attorney, Agent, or Firm* — Browdy and Neimark, PLLC

(57) ABSTRACT

The invention relates to tPA mutant devoid of protease activity and uses thereof in compositions and methods for the treatment and prevention of pathologic conditions involving neurological injury or an ischemic disease or condition. More specifically, the invention relates to a Ser[481] to Ala mutant of tPA and to compositions and combinations thereof for the treatment of stroke, acute brain injury and neurodegenerative disorders. The invention further provides methods and kits for the treatment of said disorders.

20 Claims, 6 Drawing Sheets

(56) References Cited

OTHER PUBLICATIONS

Figure 1:
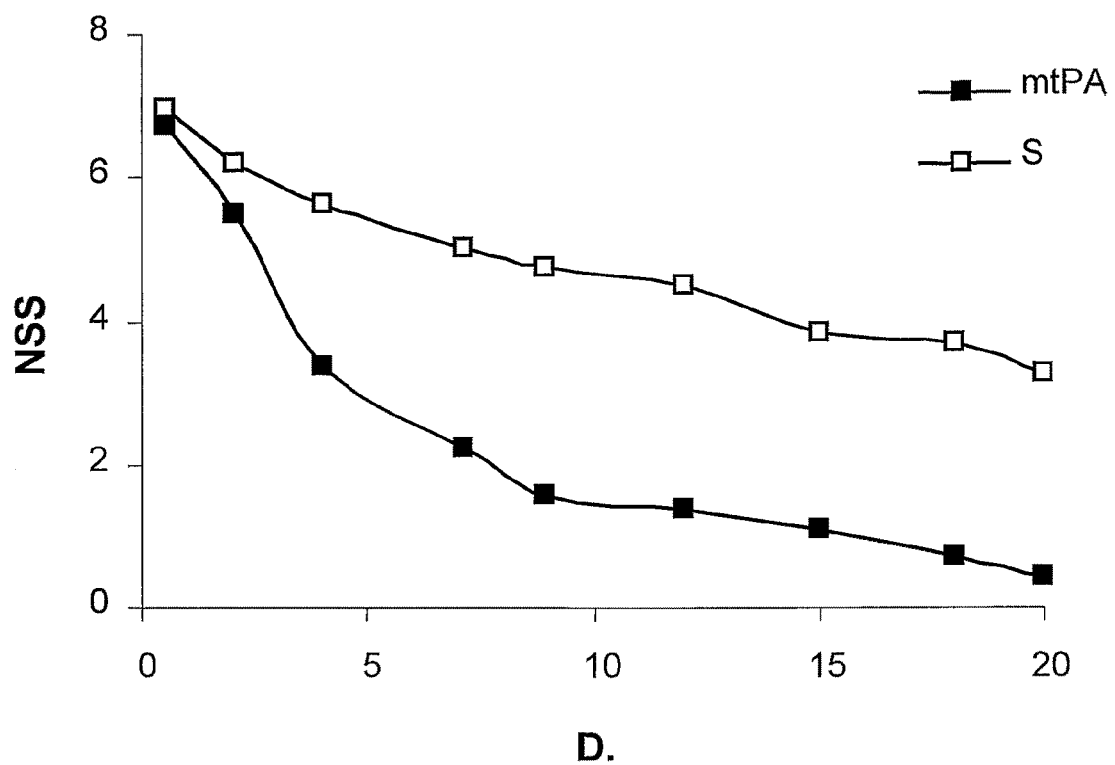

Database Genbank NCBI: Mar. 31, 1995, Siebert, P.D. and Fong, K.: "plasminogen activator preprotein [Homo sapiens]" XP002538298, Database access No. CAA31489.

Bennett W.F. Jour. Biol. Chem. 266(8):5191-5201 (1991).

Yi et al., Infarct reduction in rats following intraventicular administration of either tissue plasminogen activator (tPA) or its non-protease mutant S478A-tPA, Experimental Neurology, 189 (2004) 354-360—7 pages.

Kim et al, Nonproteolytic neuroprotection by human recombinant tissue plasminogen activator, Science 284, 647 (1990)—6 pages.

Flierl et al., Mouse closed head injury mode induced by a weight drop device, Published on-line Aug. 27, 2009, doi: 10.1038/nprot2009.148—10 pages.

Werner et al., Pathophysiology of traumatic brain injury, British Journal of Anaesthesia 99(i): 4-9 (2007)—6 pages.

Mans et al., EBIC-Guidelines for Management of Severe Head Injury in Adults, Acta Neuochir (Wien) (1997) 139: 286-294—9 pages.

Chen et al., Patients with traumatic brain injury: Population-based study suggests increased rick of stroke, Stroke 2011:42: 2733-2739—8 pages.

Collen et al.; Thrombolytic agents; Thromb. Haemost; 93:627-30 (2005).

Bennett et al.; High resolution analysis of functional determinants on human tissue-type plasminogen activator; Jour. Biol. Chem. 8:5191-5201 (1991).

Stein et al.; Association between intravascular microthrombosis and cerebral ischemia in traumatic brain injury; Neurosurgery 54:687-681(2004).

* cited by examiner

TPA MUTANT IN THE TREATMENT OF ACUTE BRAIN INJURY AND NEURODEGENERATIVE DISORDERS

REFERENCE TO CO-PENDING APPLICATIONS

Priority is claimed as a 371 of international of PCT/IL2009/000300, filed on Mar. 16, 2009, which claims priority to Israeli patent application number 190184 filed on Mar. 16, 2008.

FIELD OF THE INVENTION

The invention relates to compositions and methods in the treatment, amelioration, and prevention of conditions involving neuronal damage. More particularly, the invention relates to tPA mutant devoid of protease activity and uses thereof in compositions and methods for the treatment and prevention of stroke, acute brain injury and neurodegenerative disorders.

BACKGROUND OF THE INVENTION

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

Traumatic brain injury (TBI) is a major cause of death and severe disability, with an estimated incidence of 1.5 million new cases per year in the United States, unfortunately resulting in 50,000 fatalities. A total of 5.3 million Americans, approximately 2% of the U.S. population, currently live with disabilities resulting from TBI. Activation of coagulation within the central nervous system (CNS) is an early and nearly universal event accompanying severe TBI. The brain is rich in tissue factor, the initiator of the coagulation cascade [Goodnight, S. H. et al. N. Engl. J. Med. 290:1043-1047 (1974)], which is released in response to TBI. Clot formation in the systemic circulation is evident within minutes and likely occurs even earlier at the site of injury [Stein, S. C. et al. J. Neurosurg. 97:1373-1377 (2002)]. There is a strong correlation between the extent to which coagulation is activated, the development of progressive changes seen on CT scan, and the likelihood of an adverse outcome, that is not dependent on the severity of the injury alone [Stein, S. C. et al. Neurosurgery 32:25-30; discussion 30-21(1993)]. Indeed, severe coagulopathy is second only to shock as an independent predictor of adverse outcome.

Plasminogen activators are enzymes that activate the zymogen plasminogen to generate the serine proteinase plasmin, which degrades fibrin. Among the plasminogen activators studied are streptokinase, urokinase and human tissue plasminogen activator (tPA) and dismutase.

Tissue type plasminogen activator (tPA) a multidomain, glycosylated, serine protease is a fibrin specific activator of plasminogen and a very effective thrombolytic agent. tPA is a protein whose primary application is in the treatment of heart attack and stroke patients. First characterized in 1979, as an important and potent biological pharmaceutical agent in the treatment of various vascular diseases due to its high fibrin specificity and potent ability to dissolve blood clots in vivo. Beechem Laboratories clot dissolving product-anisoylated plasminogenstreptokinase activator complex, trade named, Eminase, is claimed to reduce the death rate in heart attack victims by 50%. Gene Tech's TPA (Activase), is also highly effective in dissolving blood clots.

Natural tPA has a plasma half-life of about six minutes or less. Due to its rapid clearance from the circulation, tPA has to be infused to achieve thrombolysis. Front loaded dosing with increased concentrations of tPA has shown more rapid and complete lysis compared to the standard infusion protocol and early potency is correlated with improved survival rate.

Plasminogen Activators and TBI

The continued existence of fibrin clots is regulated not only by exposure of tissue factor, but also by the fibrinolytic system. Fibrin is lysed by plasmin. Plasmin is formed from the proenzyme plasminogen through cleavage of a single peptide bond, primarily by tissue type (tPA) or urokinase type (uPA) plasminogen activator. The activity of plasmin is restrained by the formation of enzymatically inactive complexes with the circulating inhibitor $\alpha_2$-antiplasmin, while tPA and uPA are regulated in a similar manner by forming complexes with plasminogen activator inhibitor-1 (PAI-1). These complexes are rapidly cleared from the circulation by the LDL receptor-related protein (LRP).

Transgenic mice deficient in endogenous tPA ($tPA^{-/-}$) have the propensity to accumulate fibrin spontaneously [Carmeliet, P. et al. Nature, 369:419-424 (1994)] and are less able to lyse clots added exogenously [Carmeliet, P. et al. (1994) Ibid.; Bdeir, K. et al. Blood, 96:1820-1826 (2000)]. Yet, $tPA^{-/-}$ mice exhibit smaller cortical lesions and less edema after TBI and have smaller lesions and better recovery of neurological function after spinal injury [Abe, Y. et al. Journal of Neurotrauma, 20:43-57 (2003)] than WT mice. In models of stroke initiated by mechanical occlusion, the size of the infarcted area in $tPA^{-/-}$ mice is also smaller than in WT animals [Wang, Y. et al. Nat Med, 4:228-231 (1998)], whereas in models characterized by cerebral thrombosis tPA deficiency exacerbates cerebrovascular fibrin deposition and CNS injury [Tabrizi, P. et al. Arterioscler. Thromb. Vasc. Biol., 19:2801-2806 (1999)]. These observations suggest that tPA may have deleterious effects on CNS function in the setting of TBI, notwithstanding the benefit attributable to its fibrinolytic activity.

Cerebral Vasoactivity of tPA and its Possible Neurotoxic Effects

The present inventors have previously reported that IV injection of tPA decreases cerebral vascular resistance in rats, and therefore tPA alters vascular tone. The inventors have previously found that high concentrations (>20 nM) of tPA stimulate the contraction of isolated aortic rings and increase systemic blood pressure in rats [Nassar, T. et al. Blood, 103:897-902 (2004)]. In contrast, tPA at these and all concentrations tested induced vasorelaxation in the cerebral circulation of pigs and rats. The ensuing decrease in cerebral vascular resistance (CVR) may be linked to the development of cerebral edema, one of the more serious complications of stroke and revascularization of ischemic areas induced by tPA. In support of this notion is the finding that $tPA^{-/-}$ mice develop less brain edema after TBI.

NMDA Receptor in TBI and Effect of tPA on Cerebral Hemodynamics

The N-methyl-D-aspartate receptor (NMDA) is an ionotropic receptor that binds the excitatory amino acid transmitter glutamine. Activation of NMDA-R elicits cerebral vasodilation and may represent a mechanism that couples local metabolism to blood flow [Faraci, F. B., K R. Circulation Research. 1993, 72:476-480 (1993)]. All glutamate receptor subtypes have been implicated in neurotoxicity. However, the NMDA subtype is thought to play a crucial role in excitotoxic neuronal cell death [Choi, D. Journal of Neurobiology, 23:1261-1276 (1992)]. Glutamatergic system hyperactivity has been demonstrated in animal models of TBI, and NMDA-R antagonists protect against experimental brain injury [Katayama Y, B. D. et al. Journal of Neurosurgery, 73:889-900 (1990); Kawamata, T. K. et al. Journal of Cerebral Blood Flow and Metabolism, 12:12-24 (1992)]. tPA is reported to signal within the CNS by cleaving the NR-1 subunit of NMDA-R [Nicole O, D. F. et al. Nat. Med., 7:59-64 (2001)].

In earlier studies, the inventors examined the role played by the glutamate NMDA receptor (NMDA-R) in tPA-mediated CNS injury post-TBI. The results of these experiments showed that the PAI-1 derived peptide EEIIMD (also denoted by SEQ ID NO. 3) inhibits the NMDA-R mediated vasoactivity including that post TBI.

Taking into consideration that tPA exerts its effect on the NMDA-R by cleaving its NR-1 subunit, the inventors speculated that mutant tPA that lacks the catalytic activity, may compete with the endogenous tPA that is released and reaches high concentrations in the CSF during TBI. This competitive effect may reduce or even prevent tPA induced neurotoxicity.

Figure 2:
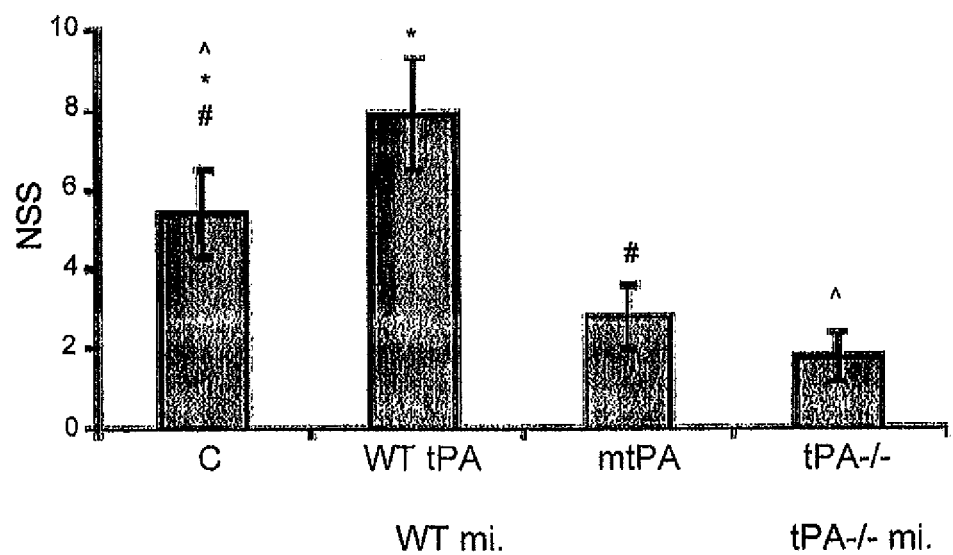

Moreover, tPA is known as having a limited therapeutic-window, when used for therapy. Specifically, tPA improves the clinical outcome in patients, but only if administered within three hours of the onset of an ischemic stroke in human patients. In addition to its brief therapeutic window, the need for radiological definition of stroke size and etiology and the increased incidence of symptomatic intracerebral hemorrhage (ICH) has constrained its clinical use. Furthermore, as also indicated above, several studies suggest that tPA may increase (directly or indirectly) post-stroke neuronal degeneration. In contrast, the mutated tPA molecule of the invention demonstrates no limited therapeutic window. As shown by FIG. 2, administration of the mutated tPA molecule of the invention to CHI animal model even two hours (corresponds to ten hours in human), resulted in significant beneficial neuroprotective effect as reflected by improved NSS, specifically as compared to saline controls and to the deleterious effect of the WT tPA on the NSS outcome.

Alterations in glutamate production may further contribute to secondary head injury. Glutamate levels, increased clinically after TBI [Choi, D. (1992) Ibid.; Katayama Y, B. D. et al. (1990) Ibid.], may affect other paths related to secondary head injury including the initiation of apoptosis by activation of NMDA-R, calcium dependent production of nitric oxide and development of superoxides and free radical damage to DNA and cellular membranes. Intact blood brain barrier (BBB) after TBI or stroke may contribute to accumulation of glutamate and is assumed to have a deleterious effect on brain function. tPA increases the permeability of the BBB and thus facilitates the clearance of neurotoxic agents such as glutamate. This effect of tPA on BBB is mediated through the LRP (LDL receptor-related protein is LRP) and has been shown by others as requiring its catalytic activity.

Surprisingly, and in contrast to Yepes et al. [Yepes et al. J. Clin. Invest. 112:1533-1540 (2003)], the inventors have now found that the mutated tPA molecule of the invention lacking any catalytic activity is still capable of mimicking some of the extracatlytic activities of WT tPA, particularly that of increasing the permeability of the BBB. Thus, clearly showing for the first time that the effect of tPA on reducing the integrity of the BBB, is not related to its catalytic activity. This mutant has been shown by the inventors as promoting the clearance of the neurotoxic amino acid glutamate and of lactate from the CSF, and thereby impeding their accumulation post TBI and also augmenting the salutary effect of the mutant on neurological outcome. These results raises the possibility that transient disruption of the BBB in the area of injury by the mutant tPA contributes directly to the improved outcome of TBI. That stands in opposition to widely accepted views in the field.

The object of the present invention therefore, is to provide a mutated tPA molecule devoid of serine protease catalytic activity, having ability to increase permeability of the BBB, and thereby facilitating the clearance of neurotoxic amino acids and of lactate, as a safe molecule having a wide therapeutic-window, for use in the treatment, amelioration and prevention of stroke and conditions involving neuronal damage, more particularly, acute brain injury and neurodegenerative disorders.

These and other objects of the invention will become clearer as the description proceeds.

SUMMARY OF THE INVENTION

In a first aspect the invention relates to a tPA mutated molecule devoid of total or partial protease activity, or any functional fragments or peptides thereof. In one embodiment, the mutated molecule carries at least one point mutation located at any position of residues Ser481, His325, Asp374, Asp475 Ser500 and Gly502 and any combinations thereof. According to another embodiment, the mutated molecule carries a point mutation in Ser481 to Ala. A specific example for such mutant is provided by a mutant having the amino acid sequence as denoted by SEQ ID No. 1.

In a second aspect, the invention relates to a pharmaceutical composition for the treatment, amelioration, or prophylaxis of a pathologic condition involving neurological injury, or an ischemic disease or condition, said composition comprises as an active ingredient a therapeutically effective amount of at least one tPA mutated molecule devoid total or partial protease activity or any functional fragments or peptides thereof, and optionally any further pharmaceutically acceptable carrier, diluent, excipient and/or additive. The composition of the invention may optionally further comprise an additional therapeutic agent, specifically, a glutamate scavenger compound.

In another aspect the invention relates to a method for the treatment, amelioration or prophylaxis of a pathologic condition involving neurological injury or an ischemic disease or condition, said method comprises the step of administering to a subject in need thereof, a therapeutically effective amount of at least one tPA mutated molecule devoid of total or partial serine protease activity or any functional fragments or peptides thereof, or any composition comprising the same or any combinations thereof, specifically, combinations with a therapeutic agent such as glutamate scavenger molecule.

A further aspect of the invention relates to the use of a therapeutically effective amount of a tPA mutated molecule devoid of total or partial serine protease activity, or any functional fragments or peptides thereof, in the preparation of a pharmaceutical composition for the treatment, amelioration or prophylaxis of a pathologic condition involving neurological injury or an ischemic disease or condition.

The invention further provides a tPA mutated molecule devoid of serine protease activity, or any functional fragments or peptides thereof, for treating a pathologic condition involving neurological injury or an ischemic disease or condition.

In another aspect, the invention relates to a pharmaceutical unit dosage form comprising at least one tPA mutated molecule devoid of serine protease activity or any functional fragments or peptides thereof or any combination or mixture thereof, or a pharmaceutically acceptable derivative thereof, and optionally at least one glutamate scavenger selected from the group consisting of glutamate-pyruvate transaminase (GPT), glutamate-oxaloacetate transaminase (GOT), Glucagon, Insulin or any combination thereof, and a pharmaceutically acceptable carrier or diluent.

Another aspect of the invention relates to a kit for achieving a therapeutic effect in a subject in need thereof comprising:

(a) at least one tPA mutated molecule devoid of serine protease activity or any functional fragments or peptides thereof or any combination or mixture thereof, or a pharmaceutically acceptable derivative thereof and a pharmaceutically acceptable carrier or diluent in a first unit dosage form;

(b) at least one glutamate scavenger selected from the group consisting of glutamate-pyruvate transaminase (GPT), glutamate-oxaloacetate transaminase (GOT), Glucagon, Insulin or any combination thereof and a pharmaceutically acceptable carrier or diluent in a second unit dosage form; and (c) container means for containing said first and second dosage forms.

These and other aspects of the invention will become apparent by the hand of the following examples.

BRIEF DESCRIPTION OF THE INVENTION

FIG. 1. Mutant tPA significantly improves the outcome in CHI model.

Figure represents the neurological severity score (NSS) of closed head injury (CHI) model animals injected intraperitoneally (ip) with mutant tPA (100 μg/mice) in saline or saline alone two hours after the head trauma.

Abbreviations: m (mutant), S (saline), NSS (neurological severity score).

FIG. 2. Mutant tPA significantly improves the outcome in CHI model compares to WT tPA and saline.

CHI WT mice were injected intraperitoneally (ip) with mutant tPA (mtPA), or WT tPA (100 μg/mice) in saline or, saline alone, two hours after the head trauma. tPA knockout mice (tPA−/−) were used as a control for endogenous WT tPA. The figure shows a histogram summarizing the NSS at day 20 after CHI. The mean±SEM of 16-18 animals/group are shown.

Abbreviations: C (control), WT (wild type), m (mutant), mi. (mice), NSS (neurological severity score).

Figure 3:
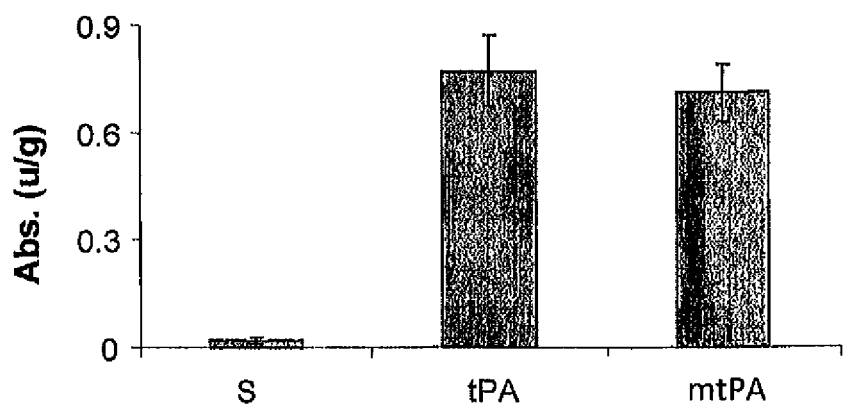

FIG. 3. Mutant tPA permeabilize the BBB

The uptake of Evans blue dye into a brain tissue served as a marker to for quantifying disruption of the blood-brain barrier and increase in permeability of the BBB. The figure shows histogram illustrating the absorbance of Evans blue injected with saline or saline containing tPA or tPA mutant. Data was expressed as absorbance at 620 nM per gram of tissue. The mean±SEM of data from 8-9 animals/group are shown.

Abbreviations: m (mutant), S (saline), Abs (Absorbance).

Figure 4A:
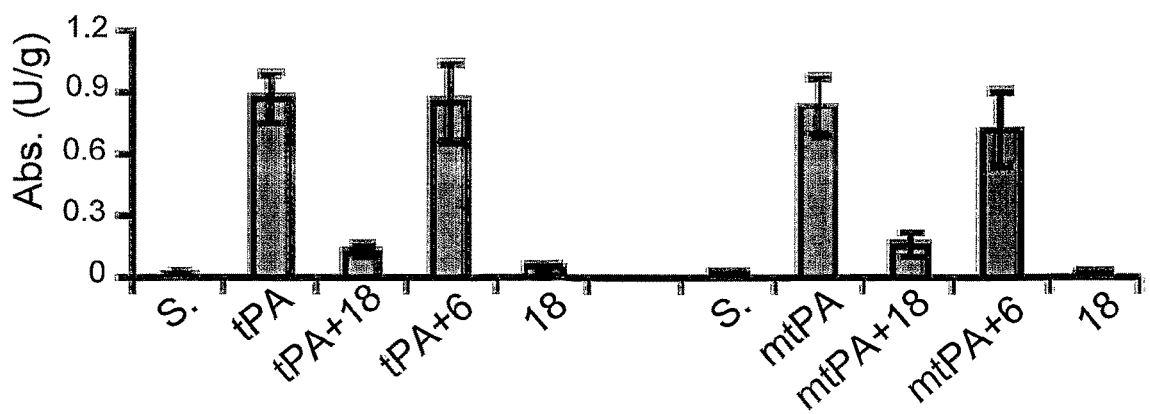
Figure 4B:

FIG. 4A-4B. Effect of PAI-1 derived peptides on BBB permeability induced by mutant tPA FIG. 4A. Mice were injected i.p. with 25 μl of saline or saline containing either WT-tPA or mtPA (1 mg/kg each) alone or together with PAI-1 derived 18 amino acids (aa) (as denoted by SEQ ID NO. 8) or 6 aa (as denoted by SEQ ID NO. 3) peptides (1 mg/kg each). Ten minutes later, the mice were given an i.v. injection of 2% Evans blue (EB) in saline. One hour after injection of dye, organs were cleared of blood by transcardiac perfusion. The brains were removed, photographed, weighed, homogenized in N,N-dimethylformamide and centrifuged. Extruded dye was quantified by absorbance at 620 nm. The figure presents a histogram illustration of the absorbance of EB at 620 nM per gram of tissue. The mean±SEM of data from 8-9 animals/group is shown.

FIG. 4B. A typical distribution of the EB after CHI. Abbreviations: S (saline), 18 (18 aa peptide, as denoted by SEQ ID NO. 8), 6 (6 aa peptide, as denoted by SEQ ID NO. 8), Abs (Absorbance).

Figure 5:
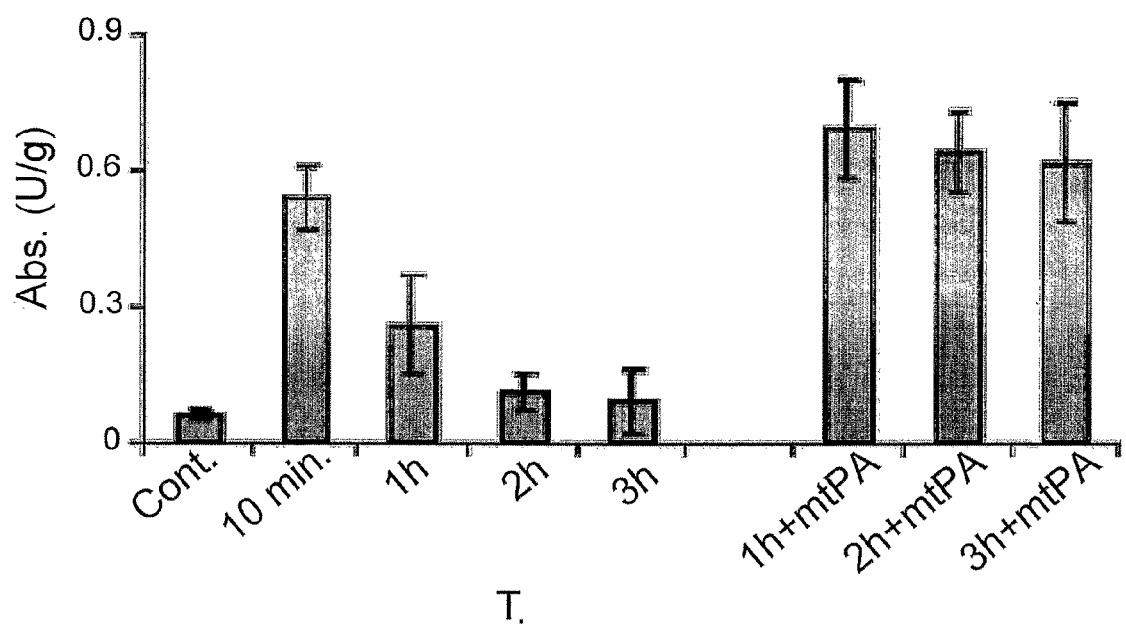

FIG. 5. Prolonged duration of blood brain barrier (BBB) permeability after CHI by the tPA mutant Mice were treated with i.p. injection of mtPA 1, 2 or 3 hours after CHI. Five minutes after mtPA injection, the animals were given an IV injection of 2% Evans blue (EB) in saline. Extravasation of EB was measured one hour after injection of the dye. The figure presents a histogram illustration of the absorbance of EB at 620 nM per gram of tissue. The mean±SEM of data from 8-9 animals/group is shown. Abbreviations: Abs (Absorbance), T (time), h (hour), min. (minutes).

Figure 6A:
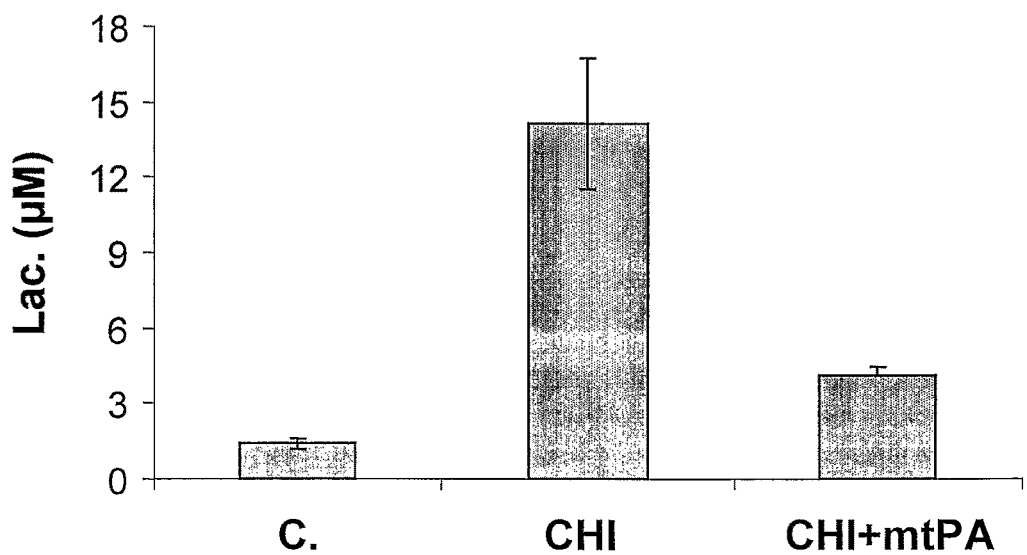
Figure 6B:
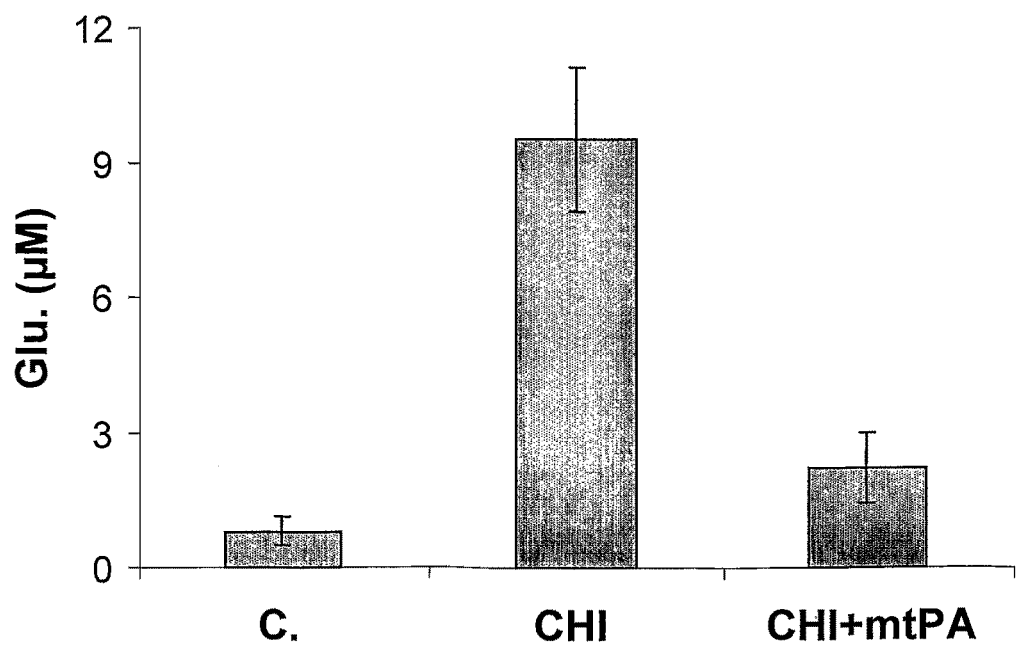

FIG. 6A-6B Mutant tPA facilitates the clearance of neurotoxic agents during head injury.

FIG. 6 shows histograms illustrating the levels of lactate (FIG. 6A) and glutamate (FIG. 6B) in CSF samples obtained from mice injected with mutant tPA, (100 μg/mice) in saline or saline alone intraperitoneally (ip), 2 hours after CHI. Mice that did not undergo CHI served as controls Abbreviations: Lac (Lactate), Glu (Glutamate), C (control) CHI (closed head injury).

Figure 7:
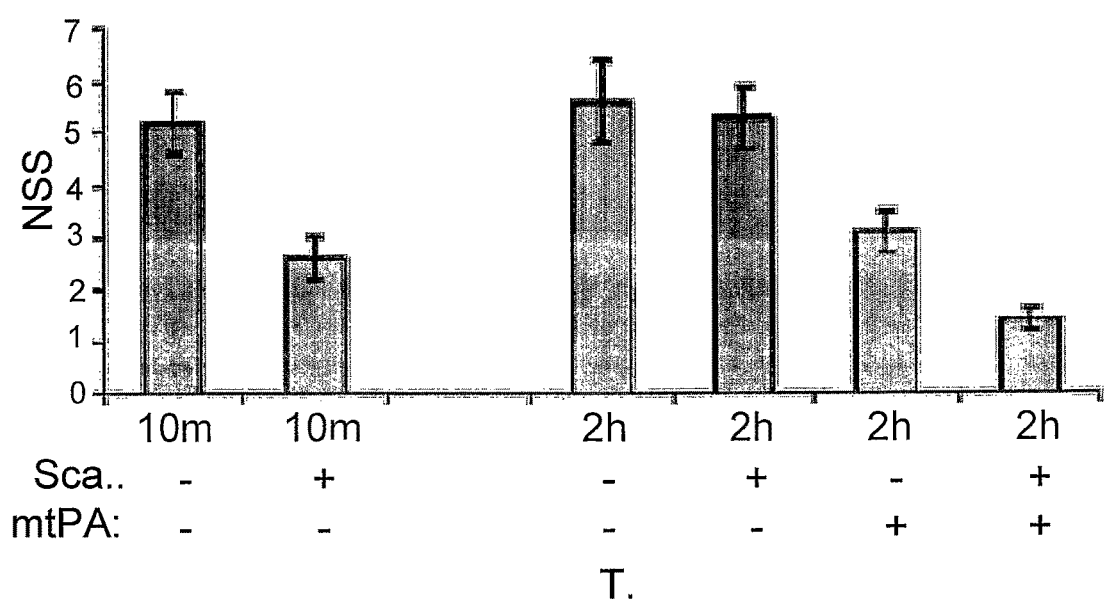

FIG. 7. Neuroprotective effect of combined administration of mutant tPA and glutamate scavenger Mice were injected i.v. with a scavenger comprising Oxaloacetate (0.005 mmol/100 g mice) and recombinant GOT (0.14 nmol/100 g) 10 min or 2 hours after CHI. 1 mg/kg mtPA was administered 2 hours after CHI alone or with the scavenger. The Figure shows the NSS on day 20 (mean±SEM of 16-18 animals/group).

Abbreviations: T (time), m (minute), h (hour) sca (scavenger), NSS (neurological severity score).

DETAILED DESCRIPTION OF THE INVENTION

It is to be understood that the invention is not limited in its application to the details set forth in the following description or illustrated in the drawings. The invention is capable of other embodiments or of being practiced out in various ways. Also, it is to be understood that the phraseology and terminology employed herein is for the purpose of description and should not be regarded as limiting.

In a first aspect, the invention relates to a tPA mutated molecule devoid of total or partial protease activity, specifically, serine protease activity, or any functional fragments or peptides thereof.

Tissue type plasminogen activator (tPA) a multidomain, glycosylated, serine protease is a fibrin specific activator of plasminogen and a very effective thrombolytic agent. It should be appreciated that "mutated tPA" or "mtPA" as used herein includes a mutated native tPA and recombinant mutated tPA, as well as modified forms of tPA that is devoid of the enzymatic activities of native tPA. More specifically, as used herein in the specification and in the claims section below, the term "devoid of protease or serine protease catalytic activity" and its derivatives refers to a mutated tPA molecule having impaired, decreased or reduced expression of activity. A preferred mutated tPA molecule lacks any catalytic activity. According to one embodiment of the present invention at least about 10-100%, more specifically, about 10%, 15%, 20%, 25%, 30%, 35%, 40%, 45%, 50%, 55%, 60%, 65%, 70%, 75%, 80%, 85%, 90%, 95%, 99% and even 100% of the tPA activity is abolished by the point mutation performed by the invention, as compared to the WT (wild type) tPA activity. It should be noted that the enzymatic activity of tPA can be measured by assessing the ability of the molecule to convert plasminogen to plasmin.

According to a specific embodiment, the mutated tPA molecule of the invention carries at least one mutation selected from the group consisting of point mutations, missense, nonsense, insertions, deletions or rearrangement. In a specific embodiment, the tPA molecule of the invention carries a point mutation.

In one embodiment, the mutated molecule carries at least one point mutation located at any position of residues Ser481, His325, Asp374, Asp475 Ser500 and Gly502 and any combinations thereof. According to another embodiment, the mutated molecule carries a point mutation in Ser481 to Ala. A specific example for such mutant is provided by a mutant having the amino acid sequence as denoted by SEQ ID NO. 1. It should be indicated that this mutated tPA molecule of the invention is designated tPA-S481A or tPA-S$^{481}$A and in some embodiments the mutated molecule is referred to as mtPA. It should be noted that this particular mutated molecule carries two additional N-terminal amino acid residues (RS) introduced for the purpose of cloning. Therefore, the invention provides a mutated tPA molecule comprising both RS residues as shown by SEQ ID NO. 1. The invention further provides a mutated tPA molecule, having a part of SEQ ID NO. 1, for example, with no additional RS.

By "fragments or peptides" it is meant a fraction of said tPA molecule. A "fragment" of a molecule, such as any of the amino acid sequences of the present invention, is meant to refer to any amino acid subset of the mutated tPA molecule. This may also include "variants" or "derivatives" thereof. A "peptide" is meant to refer to a particular amino acid subset having functional activity. By "functional" is meant having the same biological function, for example, having the ability of increasing permeability of the BBB and thereby facilitating clearance of neurotoxic amino acids, or having the ability of competing with the WT tPA and thereby inhibiting the activation of NMDA-R by tPA. A "variant" of such molecule is meant to refer a naturally occurring molecule substantially similar to either the entire molecule or a fragment thereof. The term "derivatives" as used herein mean a molecule comprising the amino acid sequence of the mutated tPA molecule, as denoted by SEQ ID NO. 1, with any insertions, deletions, substitutions and modifications that do not interfere with the ability of said molecule to increase the permeability of the BBB and thereby facilitates clearance of neurotoxic amino acids, or alternatively or additionally, to recognize the NR-1 cleavage site of NMDA-R, compete with the wild type tPA molecule and thereby inhibit NMDA-R activation. A derivative should maintain a minimal homology to said amino acid sequence, e.g. even less than 30%, preferably, 90% to 40% homology, 80% to 50% or 70% to 60%. It should be appreciated that the terms "insertions" and "deletions" are meant any addition or reduction, respectively, of amino acid residues to the mutated tPA peptide used by the invention, between 1 to 50 amino acid residues, preferably, between 1 to 20 amino acid residues and most preferably, between 1 to 10 amino acid residues. More particularly, insertions or deletions, respectively, may include addition or reduction of 1, 2, 3, 4, 5, 6, 7, 8, 9 or 10 amino acid residues to the mutated tPA molecule of SEQ ID NO. 1. A specific embodiment for such derivative is a mutated molecule with no additional RS residues at the N-terminal end of the molecule.

The amino acid L-glutamic acid (glutamate), mediates many of the excitatory signals between neurons in the central nervous system. Under normal conditions, accumulation of glutamate in the extracellular space is prevented by the operation of a recycling mechanism that serves to maintain neuronal glutamate levels despite continual loss through transmitter release. Glutamate, released by glutamatergic neurons, is taken up into glial cells where it is converted into glutamine. Glutamine reenters the neurons and is hydrolyzed by glutaminase to form glutamate, thus replenishing the neurotransmitter pool.

This biochemical pathway also serves as an endogenous neuroprotective mechanism, which functions by removing the synaptically released glutamate from the extracellular space and converting it to the nontoxic amino acid glutamine before toxicity occurs. The excitotoxic potential of glutamate (i.e., defined as the ability of excess glutamate to overexcite neurons and cause their death) is held in check as long as the transport process is functioning properly. However, failure or reduction in the transport process such as under ischemic conditions, results in accumulation of glutamate in the extracellular synaptic fluid and excessive stimulation of excitatory receptors, a situation that leads to neuronal death. Two additional factors enhance glutamate accumulation, (i) over stimulated neurons begin to release excessive quantities of glutamate at additional synaptic junctions, which causes even more neurons to become over stimulated, drawing them into a neurotoxic cascade that reaches beyond the initial zone of ischemia; and, (ii) over stimulated neurons begin utilizing any available supplies of glucose or oxygen even faster than normal, which leads to accelerated depletion of these limited energy resources and further impairment of the glutamate transport process. This biochemical cascade of induction and progression may continue for hours or days and causes delayed neuronal death.

Abnormally high Glutamate levels in brain interstitial and cerebrospinal fluids are the hallmark of several neurodegenerative conditions. These include acute brain anoxia/ischemia i.e stroke, perinatal brain damage, traumatic brain injury, bacterial meningitis, subarachnoid hemorrhage, hemorrhagic shock, newly diagnosed epilepsy, migraine, stress and various chronic neurodegenerative diseases such as glaucoma, amyotrophic lateral sclerosis, HIV dementia and Alzheimer's disease.

Glutamate binds or interacts with one or more glutamate receptors which can be differentiated pharmacologically into several subtypes. In the mammalian central nervous system (CNS) there are three main subtypes of ionotropic glutamate receptors, defined pharmacologically by the selective agonists N-methyl-D-aspartate (NMDA), kainate (KA), and α-amino-3-hydroxy-5-methylisoxazole-4-propionic acid (AMPA).

Under pathological conditions of acute and chronic forms of neurodegeneration over-activation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas.

When activated by glutamate, the endogenous neurotransmitter, the NMDA receptor permits the influx of extracellular calcium ($Ca^{2+}$) and sodium ($Na^+$) through an associated ion channel. The NMDA receptor allows considerably more influx of $Ca^{2+}$ than do kainate or AMPA receptors, and is an example of a receptor-operated $Ca^{2+}$ channel. Normally, the channel is opened only briefly, allowing a localized and transient increase in the concentration of intracellular $Ca^{2+}$ ($[Ca^{2+}]_i$), which, in turn, alters the functional activity of the cell. However, prolonged increases in $[Ca^{2+}]_i$, resulting from chronic stimulation of the NMDA receptor, are toxic to the cell and lead to cell death. The chronic elevation in $[Ca^{2+}]_i$, resulting from stimulation of NMDA receptors, is considered to be a major cause of neuronal degeneration following a stroke. Overstimulation of NMDA receptors is also said to be involved in the pathogenesis of some forms of epilepsy, anxiety, neurodegenerative diseases and hyperalgesic states.

The deleterious effect of tissue plasminogen activators (tPA) on brain tissue following neurological injury and the need to find novel approaches to the treatment, amelioration or prophylaxis of pathologic conditions involving neuronal injury, have lead the present inventors to examine whether a mutated tPA molecule might be able to compete with endogenous tPA and thereby inhibit, ameliorate or prevent such pathologic conditions. It should be further noted that the mutated tPA molecule of the invention is devoid of any serine protease activity and therefore exhibiting an impaired ability (exhibiting no ability) of dissolving blood cloths. Therefore, the mutated tPA molecule of the invention provides a safe compound having reduces probability of causing an internal uncontrolled bleeding that may be caused by the WT tPA molecule.

The data shown by the present inventors indicate that by decreasing the concentration of the post TBI glutamate in the circulation, presumably by increasing permeability of the BBB, the outcome of the animals improved. Moreover, as shown by FIG. 7, treatment using glutamate scavenger compounds was ineffective when it was given after the recovery of the BBB. Only a combination of the glutamate scavenger compounds with the mutated tPA molecule of the invention resulted in increased BBB permeability, and thereby a synergistic beneficial effect on the NSS, even more than two hours after the injury occurred. Without being bound by any theory such outcomes strongly suggest that the increase in permeability of BBB by the mutant of the invention contribute to the efficiency of clearance of neurotoxic reagents.

Thus, the invention further provides a compound capable of increasing permeability and reducing the integrity of the BBB, and thereby enhancing clearance of neurotoxic agents. Blood-brain barrier (BBB) is a membranic structure that acts primarily to protect the brain from chemicals in the blood, while still allowing essential metabolic function. It is composed of endothelial cells, which are packed very tightly in brain capillaries. This higher density restricts passage of substances from the bloodstream much more than endothelial cells in capillaries elsewhere in the body. Astrocyte cell projections called astrocytic feet (also known as "glial limitans") surround the endothelial cells of the BBB, providing biochemical support to those cells.

According to one embodiment, the mutated tPA molecule of the invention is capable of decreasing the integrity, increasing the permeability or "opening" of a blood brain barrier in about 10-95% as compared to a control. According to one embodiment, control is the integrity, permeabilization or the BBB opening, after CHI, in the absence of the tPA mutated molecule. According to another embodiment, control is the integrity or permeability of the BBB, before the CHI occurred. More specifically, the mutated tPA molecule of the invention is capable of increasing the permeability of the BBB in about 10%, 15%, 20%, 25%, 30%, 35%, 40%, 45%, 50%, 55%, 60%, 65%, 70%, 75%, 80%, 85%, 90%, 95% and even 99% as compared to control. It should be noted that the increase in BBB permeability results in a corresponding decrease in accumulation of neurotoxic agents in the injured tissue. More specifically, such reduction may be of about 10%, 15%, 20%, 25%, 30%, 35%, 40%, 45%, 50%, 55%, 60%, 65%, 70%, 75%, 80%, 85%, 90%, 95% and even 99% as compared to control.

According to one embodiment, such compound may be a mutated tPA molecule devoid of serine protease activity, or any functional fragments or peptides thereof. As shown by the invention, this mutant is capable of increasing permeability of the BBB, and thereby enhancing clearance of neurotoxic agents. As shown by FIG. 5, the mutated tPA molecule of the invention increases BBB permeability even when injected three hours after the occurrence of the injury. These results clearly indicate that the mutated tPA molecule of the invention is a safe drug, as being devoid of blood cloths dissolving properties, and is an effective drug, having a wide therapeutic window. Therapeutic window as used herein is meant that the mutated tPA molecule of the invention is effective in increasing BBB permeability and reducing NSS when administered between 10 minutes to several days after the occurrence of the injury. More specifically, the mutated molecule of the invention is effective when administered to an injured subject after 10', 20', 30', 45', 50', 60', 90', 150', 180', 4 hr, 5 hr, 6 hr, 7 hr, 8 hr, 9 hr, 10 hr, 11 hr, 12 hr, 13 hr, 14 hr, 15 hr, 16 hr, 17 hr, 18 hr, 19 hr, 20 hr, 21 hr, 22 hr, 23 hr, 24 hr, 2 days, 3 days 4 days, 5 days, 6 days and even 7 days or more after the occurrence of the injury.

It should be appreciated that the invention further encompasses the use of the mutated tPA molecule of the invention for facilitating the delivery of different drugs to a target brain tissue by increasing permeability of the BBB.

In yet another embodiment, the mutated tPA molecule of the invention exhibits a beneficial therapeutic effect on head injury as reflected by reduction of the NSS. As indicated herein, such reduction or decrease may be of about 10 to 95%, specifically, about 10%; 15%, 20%, 25%, 30%, 35%, 40%, 45%, 50%, 55%, 60%, 65%, 70%, 75%, 80%, 85%, 90%, 95% and even 99% of the NSS in a subject in need thereof.

Furthermore, without being bound by any theory, the mutated tPA molecule may exert its neuroprotective effect by preventing the activation of NMDA-R by the WT tPA. Moreover, the possible mechanism by which tPA exerts its neurotoxic effect through activation of NMDA-R, raises the possibility of identifying compounds inhibiting the activation of NMDA-R by tPA, as potential therapeutic approach.

According to a specific embodiment of this aspect, the tPA mutated molecule or fragments thereof is capable of inhibiting tPA activation of NMDA-R.

Thus, the invention further provides a compound capable of inhibiting the activation of N-methyl-D-aspartate receptor (NMDA-R) by tPA (tissue plasminogen activator) for the treatment, amelioration or prophylaxis of NMDA-R-mediated disorders.

As used herein, NMDA-R-mediated disorders may be any one of acute forms of neurodegeneration or anoxia/ischemia conditions caused, e.g., by stroke, perinatal brain damage, traumatic brain injury, bacterial meningitis, subarachnoid hemorrhage, hemorrhagic shock, newly diagnosed epilepsy, anxiety, migraine, stress and various chronic neurodegenerative disorders such as Alzheimer's disease, Parkinson's disease, Huntington's disease, ALS (amyotrophic lateral sclerosis), glaucoma, amyotrophic lateral sclerosis, HIV dementia, hyperalgesic states and neurodegeneration associated with bacterial or viral infections, or depression and chronic and acute pain.

According to one embodiment, the compound of the invention may be a mutated tPA molecule devoid of serine protease activity, or any functional fragments or peptides thereof capable of inhibiting NMDA-R activation and thereby inhibit, ameliorate or prevent NMDA-R mediated disorders.

More specifically, such mutant may be the mutated molecule of the invention.

Alterations in glutamate production contribute to aspects of secondary head injury. Glutamate levels are increased clinically after TBI [Choi, (1992) ibid.; Katayama (1990) ibid.] and affect other paths of secondary head injury, including activation of apoptosis by activation of NMDA-R, calcium dependent production of nitric oxide and development of superoxides and free radical damage to DNA and cellular membranes [Kawamata (1992) ibid.; LaPlaca (1998) ibid.].

According to another aspect, the invention provides a composition comprising at least one tPA (tissue plasminogen activator) mutated molecule devoid of serine protease activity or any functional fragments or peptides thereof. The composition of the invention optionally further comprises an additional therapeutic agent. It should be further noted that the composition of the invention, further comprises any pharmaceutically acceptable carrier excipient or diluent.

According to one embodiment, the additional therapeutic agent comprised within the composition of the invention may be at least one glutamate scavenger compound, specifically, a glutamate scavenger selected from the group consisting of glutamate-pyruvate transaminase (GPT), glutamate-oxaloacetate transaminase (GOT), Insulin, Glucagon or any composition or combination thereof. In one specific embodiment, the glutamate scavenger is at least one of glutamate-pyruvate transaminase (GPT) and glutamate-oxaloacetate transaminase (GOT), or any combination thereof.

In another aspect the invention relates to a pharmaceutical composition for the treatment, amelioration, or prophylaxis of a pathologic condition involving neurological injury, and an ischemic disease or condition said composition comprises as an active ingredient a therapeutically effective amount of at least one tPA mutated molecule devoid of total or partial protease activity or any functional fragments or peptides thereof, and optionally any further pharmaceutically acceptable carrier, diluent, excipient and/or additive. According to one embodiment, the composition of the invention optionally further comprises an additional therapeutic agent.

An "ischemic disease or condition" as used herein refers to a condition characterized by local inflammation resulting from an interruption in the blood supply to a tissue due to a blockage or hemorrhage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The invention thus provides a mutated tPA molecule for treating ischemic disease or condition, more specifically, for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack (TIA) is one in which the blood flow to the brain is interrupted only briefly causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption in blood flow to the brain resulting from either a thromboembolism or hemorrhage. A stroke causes a loss of neurons typically resulting in a neurologic deficit that may improve but that does not entirely resolve. Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms. The term thromboembolism will be used throughout this patent application to describe thrombotic and embolic strokes. Hemorrhagic stroke is caused by the rupture of a blood vessel in a subarachnoid space or intracerebral tissue.

Therefore, the mutated tPA molecule of the invention or any composition thereof, is particularly intended for the treatment of stroke.

In yet another embodiment, the mutated tPA molecule of the invention may be used for the treatment of heart attack.

The pharmaceutical compositions described herein may be applicable in the treatment, amelioration and prophylaxis of pathological conditions involving neurological injury such as for example acute or traumatic brain injury, brain anoxia, prenatal brain damage, global and focal ischemic and hemorrhagic stroke, head trauma, spinal cord injury, neurosurgery intervention, hypoxia-induced nerve cell damage (such as in cardiac arrest or neonatal distress), epilepsy, anxiety, and a neurodegenerative disorder.

According to a specific embodiment, the composition of the invention may be specifically applicable for treating TBI.

TBI as used herein includes those brain injuries occurring in motor vehicle accidents, after falls, caused by assault and in sports when force is applied to the head sufficiently to produce injury to the structure of the brain. Such injury can include bruising, tearing and swelling of brain tissue. It can include intracranial bleeding, such as subdural, epidural, subarachnoid, intraparenchymal and intraventricular hemorrhage. Brain tissue can be injured such as due to shearing of axons, even when little to no bleeding occurs. Despite extensive research over many years at several large clinical trials, there are currently no effective treatments for TBI other than meticulous supportive care.

One definition of TBI is provided in the Individuals with Disabilities Education Act which defines traumatic brain injury as an acquired injury to the brain caused by an external physical force, resulting in total or partial functional disability or psychosocial impairment, or both, that adversely affects a child's educational performance. The term as used herein applies to both open and closed head injuries resulting in impairments in one or more areas, such as cognition, language, memory, attention, reasoning, abstract thinking, judgment, problem-solving, sensory, perceptual, and motor abilities, psycho-social behavior, physical functions, information processing, and speech.

TBI occurs in people of all ages, including infants and children, young adults, adults and elderly. A similar definition applies to people of all ages, with the modification that work-related, cognitive, behavioral, emotional and social performance impairments can be involved in addition to adverse effects on educational performance.

Signs and symptoms of TBI include impaired cognitive function, altered behavior, emotional dysregulation, seizures, headaches, impaired nervous system structure or function, and an increased risk of development of Alzheimer's disease. Impaired cognitive function includes but is not limited to difficulties with memory, attention, concentration, abstract thought, creativity, executive, function, planning, and organization. Altered behavior includes but is not limited to physical or verbal aggression, impulsivity, decreased inhibition, apathy, decreased initiation, changes in personality, abuse of alcohol, tobacco or drugs, and other addiction-related behaviors. Emotional dysregulation includes but is not limited to depression, anxiety, mania, irritability, and emotional incontinence. Seizures include but are not limited to generalized tonic-clonic seizures, complex partial seizures, and non-epileptic, psychogenic seizures. Headaches include but are not limited to common migraine, classic migraine, complex or atypical migraine, cluster headache and tension headache. Impaired nervous system structure or function includes but is not limited to hydrocephalus, parkinsonism, sleep disorders, psychosis, impairment of balance and coordination. This includes motor impairments such as monoparesis, hemiparesis, tetraparesis, ataxia, ballismus and tremor. This also includes sensory loss or dysfunction including olfactory, tactile, gustatory, visual and auditory sensation. Furthermore, this includes autonomic nervous system impairments such as bowel and bladder dysfunction, sexual dysfunction, blood pressure and temperature dysregulation. Finally, this includes hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators. Increased risk of development of Alzheimer's disease includes that risk that is elevated over the expected risk given the patient's age, family history, genetic status and other known risk factors.

It should be noted that acute or traumatic brain injury may be any one of brain injuries occurring in motor vehicle accidents, after falls, caused by assault or in sports, said injury include bruising, tearing and swelling of brain tissue, intracranial bleeding (such as subdural, epidural, subarachnoid, intraparenchymal, and intraventricular hemorrhage), and shearing of axons.

According to another specific embodiment, the compositions of the invention may be applicable for subjects suffering of a neurodegenerative disorders or neurological disorders.

A "neurological disorder" is a disease or disorder characterized by an abnormality or malfunction of neuronal cells or neuronal support cells. The disorder can affect the central and/or peripheral nervous system. Exemplary neurological diseases include neuropathies, skeletal muscle atrophy and neurodegenerative diseases.

"Neurodegenerative disorders" are complex and pernicious diseases, their onset is followed by progressive deterioration. Clinical manifestations are determined by the location and seriousness of the disorder. Although the causes may differ, patients with neurodegenerative disorders are likely to show localized to generalized atrophy of brain cells, leading to compromises in both mental and physical function. Exemplary neurodegenerative diseases include: Alzheimer's disease, Parkinson's disease, ALS (Amyotrophic Lateral Sclerosis), Huntington's disease, taupathies such as Pick's disease, fronto temporal dementia, cortico-basal degeneration and progressive supranuclear palsy and Spongiform encephalopathies such as Scrapie, mad cow disease and Bovine spongiform encephalopathy, Creutzfeldt-Jakob disease, Fatal Familial Insomnia, Gerstmann-Straussler-Scheinker syndrome and Kuru.

Mentally, patients may exhibit forgetfulness, poor memory, decrease in mental capacities, emotional disturbances, and/or poor speech. Physically, patients may exhibit partial to complete incontinence, aspiration of food particles, tremor, poor balance, muscle rigidity, and/or muscle paralysis.

The terms "effective amount" or "sufficient amount" of the tPA mutated molecule devoid of serine protease activity, and any functional fragments or peptides thereof comprised within the pharmaceutical compositions of the invention, mean an amount necessary to achieve a selected result. The "effective treatment amount" is, determined by the severity of the disease in conjunction with the preventive or therapeutic objectives, the route of administration and the patient's general condition (age, sex, weight and other considerations known to the attending physician).

According to a specific embodiment the therapeutically effective amount of the mutated tPA molecule devoid of serine protease activity, and any functional fragments or peptides thereof, may be administered within a dosage unit form in the range from about 1 µg/kg to about 100 mg/Kg body weight, specifically, from about 10 µg/kg to about 10 mg/Kg body weight, more specifically, about 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2 mg/kg, 3 mg/kg, 4 mg/kg, 5 mg/kg, 6 mg/kg, 7 mg/kg, 8 mg/kg, 9 mg/kg and 10 mg/kg. A specific embodiment is an effective amount of about 1 mg/kg. Another specific embodiment is an effective amount of about 5 mg per Kg of body weight.

According to another embodiment, the mutated tPA molecule comprised within the pharmaceutical compositions of the invention carries at least one point mutation located at any position of residues Ser481, His325, Asp374, Asp475 Ser500 and Gly502 and any combinations thereof. According to another embodiment, the mutated molecule carries a point mutation in Ser481 to Ala. A specific example for such mutant is provided by a mutant having the amino acid sequence as denoted by SEQ ID NO. 1, designated tPA-S481A, or tPA-$S^{481}A$.

According to a specific embodiment of this aspect, the tPA mutated molecule is specifically as described by the invention.

In many instances, combination therapies employing two or more therapeutic compounds are required to adequately address the medical condition and/or effects secondary to the condition under treatment. Thus, the mutated tPA molecule of the invention can be employed alone or alternatively together with various other therapeutic agents to address a broader spectrum of brain injury abnormalities, specifically, elevating BBB permeability thereby facilitating clearance of neurotoxic reagents.

Combining two BBB permeabilizing medications safely and effectively improves overall beneficial effect on all brain injury abnormalities and reduces ischemic diseases risk factors.

According to one embodiment, the composition of the invention may comprise an additional therapeutic agent. As shown by FIG. 7, the tPA mutated molecule of the invention exhibited a synergistic beneficial effect on the NSS of CHI subjects, when combined with glutamate scavenger compounds. Therefore, in one specific embodiment the composition of the invention may comprise as an additional therapeutic agent, a glutamate scavenger selected from the group consisting of glutamate-pyruvate transaminase (GPT) and glutamate-oxaloacetate transaminase (GOT) or any composition or combination thereof. Glutamate scavenger is group of compounds increasing the efflux of the glutamate that accumulates in the brain after CHI to the blood. Plasma glutamate-pyruvate transaminase (GPT) and glutamate-oxaloacetate transaminase (GOT), transform glutamate into 2-ketoglutarate in the presence of their respective co-substrates, pyruvate and oxaloacetate.

As shown by the FIG. 3 of the following Example 2, the mutated tPA molecule of the invention is capable of increasing permeability of the BBB and thereby facilitating the clearance of neurotoxic agents such as glutamate and lactate (demonstrated by FIG. 6). The invention therefore further provides a composition for enhancing clearance of neurotoxic agents comprising as an active ingredient a mutated tPA molecule devoid of serine protease catalytic activity or any functional fragments or peptides thereof, wherein said tPA mutated molecule is capable of increasing permeability of the BBB, and thereby inhibit, ameliorate or prevent the accumulation of neurotoxic agents. Therefore, according to one embodiment, the composition of the invention is particularly applicable for increasing the permeability of the BBB (blood-brain-barrier) in a subject in need thereof. More specifically, the composition of the invention may be used for increasing the permeability or reducing the integrity of the BBB, and extending the duration of the BBB permeability for about 10 minutes to seven days after head injury, thereby facilitating the clearance of neurotoxic agents from the injured brain tissue.

According to another embodiment, the composition of the invention effectively reduces the NSS (neurological severity score) in a subject in need thereof. More specifically, the composition of the invention may lead to reduction of about 10 to 95%, specifically, about 10%, 15%, 20%, 25%, 30%, 35%, 40%, 45%, 50%, 55%, 60%, 65%, 70%, 75%, 80%, 85%, 90%, 95% and even 99% of the NSS in a subject in need thereof, as compared to untreated subjects.

In yet another specific embodiment of this aspect, the tPA mutated molecule or any functional fragments or peptides thereof may be capable of inhibiting tPA activation of NMDA-R.

Thus, the invention further provides a composition for inhibiting tPA activation of NMDA-R comprising as an active ingredient a mutated tPA molecule devoid of serine protease catalytic activity or any functional fragments or peptides thereof, wherein said tPA mutated molecule is capable of inhibiting tPA activation of NMDA-R and thereby inhibit, ameliorate or prevent NMDA-R mediated disorders. According to a specific embodiment of this aspect the tPA mutated molecule is as described by the invention.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, and especially pp. 1521-1712 therein, fully incorporated herein by reference.

Therapeutic formulations may be administered in any conventional dosage formulation. Formulations typically comprise at least one active ingredient, as defined above, together with one or more acceptable excipients, carriers thereof.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical compositions of the invention can be administered and dosed in accordance with good medical practice.

The compositions of the invention may comprise the active substance in free form and be administered directly to the subject to be treated. Formulations typically comprise at least one active ingredient, as defined above, together with one or more acceptable carriers thereof. Each carrier should be both pharmaceutically and physiologically acceptable in the sense of being compatible with the other ingredients and not injurious to the patient.

Formulations include those suitable for parenteral (including intraperitoneal (i.p.), subcutaneous (s.c.), intramuscular (i.m.), intravenous (i.v.) and intradermal), oral or nasal administration. The formulations may conveniently be presented in unit dosage form and may be prepared by any methods well known in the art of pharmacy. The nature, availability and sources, and the administration of all such compounds including the effective amounts necessary to produce desirable effects in a subject are well known in the art and need not be further described herein.

The pharmaceutical compositions of the invention generally comprise a buffering agent, an agent that adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

In instances in which oral administration is in the form of a tablet or capsule, the active drug components (immunoglobulin preparation) can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

In another aspect the invention relates to a method for the treatment, amelioration or prophylaxis of a pathologic condition involving neurological injury, or an ischemic disease or condition. The method of the invention comprises the step of administering to a subject in need thereof, a therapeutically effective amount of at least one tPA mutated molecule devoid of serine protease activity any functional fragments or peptides thereof or any compositions comprising the same or any combinations thereof with an additional therapeutic agent.

As described herein above, the invention provides pharmaceutical compositions and methods for the treatment of a pathologic condition. The terms "treat, treating, treatment" as used herein and in the claims mean ameliorating one or more clinical indicia of disease activity in a patient having a pathologic condition involving neuronal injury or a neurodegenerative disease.

"Treatment" refers to therapeutic treatment. Those in need of treatment are mammalian subjects suffering from any pathological condition involving neuronal injury. By "patient" or "subject in need" is meant any mammal for which administration of a tPA mutated molecule devoid of serine protease activity, and any functional fragments or peptides thereof, or any pharmaceutical composition comprising these compounds or derivatives thereof is desired, in order to prevent, overcome or slow down such infliction. It should be noted that the protective and therapeutic effect of the mutated tPA molecule, is clearly demonstrated in Example 1 and FIGS. 1, 2 and 7. These Examples show that treatment with the mutated tPA molecule significantly attenuates the neurological damage that follow head trauma. It should be further noted that this effect is a long term effect lasting for about more than 20 days. Moreover, the results presented by the present invention clearly demonstrate a wide therapeutic window for the mutated molecule of the invention, indicating that administration of the composition of the invention is effective even when performed between 10 minutes to 7 days after the occurrence of the injury.

To provide a "preventive treatment" or "prophylactic treatment" is acting in a protective manner, to defend against or prevent something, especially a condition or disease.

"Mammal" or "mammalian" for purposes of treatment refers to any animal classified as a mammal including, human, research animals, domestic and farm animals, and zoo, sports, or pet animals, such as dogs, horses, cats, cows, etc. In a particular embodiment said mammalian subject is a human subject.

As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

As indicated above, generally, the dosage of tPA mutated molecule devoid of serine protease activity, and any functional fragments or peptides thereof needed to achieve a therapeutic effect will depend not only on such factors as the age, weight and sex of the patient and mode of administration, but also on the degree of disease progression and the potency of the particular derivative being utilized for the particular disorder of disease concerned.

According to one preferred embodiment, pathologic condition involving neurological injury or damage may be any one of acute or traumatic brain injury, stroke, brain anoxia, prenatal brain damage, global and focal ischemic and hemorrhagic stroke, head trauma, spinal cord injury, neurosurgery intervention hypoxia-induced nerve cell damage such as in cardiac arrest or neonatal distress, epilepsy, anxiety, and a neurodegenerative disorder.

Acute or traumatic brain injury may be any one of brain injuries occurring in motor vehicle accidents, after falls, caused by assault or in sports, said injury include bruising, tearing and swelling of brain tissue, intracranial bleeding (such as subdural, epidural, subarachnoid, intraparenchymal, and intraventricular hemorrhage), and shearing of axons.

According to another embodiment, the method of the invention may be applicable for subjects suffering of a neurodegenerative disorders such as for example Alzheimer's disease, Parkinson's disease, ALS (Amyotrophic Lateral Sclerosis), Huntington's disease, taupathies such as Pick's disease, fronto temporal dementia, cortico-basal degeneration and progressive supranuclear palsy and Spongiform encephalopathies such as Scrapie, mad cow disease and Bovine spongiform encephalopathy, Creutzfeldt-Jakob disease, Fatal Familial Insomnia, Gerstmann-Straussler-Scheinker syndrome and Kuru.

Although intraperitoneal (i.p.) administration is preferred, it should be appreciated that any other route of administration may be applicable, for example, intravenous (i.v.), intramuscular (i.m.), subcutaneous (s.c.), oral, intranasal, parenteral, intravaginal, intranasal, mucosal, sublingual, topical, rectal or subcutaneous administration, or any combination thereof.

According to a preferred embodiment the mutated tPA molecule used by the method of the invention is the mutated molecule as described by the invention.

According to another embodiment the therapeutically effective amount of mutated tPA molecule devoid of serine protease activity, and any functional fragments or peptides administered by the method of the invention may range from about 1 µg/kg to about 100 mg/Kg body weight, more specifically about 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2 mg/kg, 3 mg/kg, 4 mg/kg, 5 mg/kg, 6 mg/kg, 7 mg/kg, 8 mg/kg, 9 mg/kg and 10 mg/kg. A specific embodiment is an effective amount of about 1 mg/kg. Another specific embodiment is an effective amount of about 5 mg per Kg of body weight. This effective amount is preferably comprised within a dosage unit form.

According to a specific embodiment of this aspect the tPA mutated molecule used by the method of the invention carries at least one point mutation located at any position of residues Ser481, His325, Asp374, Asp475 Ser500 and Gly502 and any combinations thereof. According to another embodiment, the mutated molecule carries a point mutation in Ser481 to Ala. A specific example for such mutant is provided by a mutant having the amino acid sequence as denoted by SEQ ID NO. 1.

As shown by the Examples, the mutated tPA molecule of the invention increases the permeability of the BBB and thereby facilitates the clearance of neurotoxic amino acids. Therefore, according to another embodiment, the tPA mutated molecule or any functional fragments or peptides thereof is capable of increasing the permeability of the BBB.

More specifically, the method of the invention may be used for increasing the permeability or reducing the integrity of the BBB, and extending the duration of the BBB permeability for about 10 minutes to seven days after head injury, thereby facilitating the clearance of neurotoxic agents from the injured brain tissue.

Thus, the invention further provides a method for enhancing clearance of neurotoxic agents from the brain of subjects suffering of post-TBI damage, said method comprises the step of administering to said subject a therapeutically effective amount of at least one mutated tPA molecule devoid of serine protease catalytic activity, any functional fragments or peptides thereof or any compositions comprising the same or any combinations thereof, with an additional therapeutic agent such as glutamate scavenger compound. It should be noted that the tPA mutated molecule is capable of increasing permeability of the BBB, and thereby inhibit, ameliorate or prevent the accumulation of neurotoxic agents.

According to one embodiment, the method of the invention effectively reduces the NSS (neurological severity score) in a subject in need thereof. More specifically, the method of the invention may lead to reduction of about 10 to 95%, specifically, about 10%, 15%, 20%, 25%, 30%, 35%, 40%, 45%, 50%, 55%, 60%, 65%, 70%, 75%, 80%, 85%, 90%, 95% and even 99% of the NSS in a subject in need thereof, as compared to untreated subjects.

According to one embodiment, the composition used by the method of the invention may comprise an additional therapeutic agent. As shown by FIG. 7, the tPA mutated molecule of the invention exhibited a synergistic beneficial effect on the NSS of CHI subjects, when combined with glutamate scavenger compounds. Therefore, in one specific embodiment the composition used by the method of the invention may comprise as an additional therapeutic agent, a glutamate scavenger selected from the group consisting of glutamate-pyruvate transaminase (GPT), glutamate-oxaloacetate transaminase (GOT), Insulin, Glucagon or any composition or combination thereof. Glutamate scavenger is group of compounds increasing the efflux of the glutamate that accumulates in the brain after CHI to the blood. Plasma glutamate-pyruvate transaminase (GPT) and glutamate-oxaloacetate transaminase (GOT), transform glutamate into 2-ketoglutarate in the presence of their respective co-substrates, pyruvate and oxaloacetate. According to a specific embodiment, the glutamate scavenger used as an additional therapeutic agent by the method of the invention may be at least one of glutamate-pyruvate transaminase (GPT), glutamate-oxaloacetate transaminase (GOT) and any combinations thereof.

In another specific embodiment of this aspect, the tPA mutated molecule or any functional fragments or peptides thereof used by the method of the invention is capable of inhibiting tPA activation of NMDA-R.

The invention therefore further provides a method for inhibiting tPA activation of NMDA-R in a subject suffering of an NMDA-R mediated disorder, said method comprises the step of administering to said subject a therapeutically effective amount of a mutated tPA molecule devoid of serine protease catalytic activity or any functional fragments or peptides thereof or of any composition thereof, wherein said tPA mutated molecule is capable of inhibiting tPA activation of NMDA-R and thereby inhibits, ameliorate, or prevents NMDA-R mediated disorders.

According to a specific embodiment, the tPA mutated molecule used by the method of the invention carried at least one point mutation located at any position of residues Ser481, His325, Asp374, Asp475 Ser500 and Gly502 and any combinations thereof. According to another embodiment, the mutated molecule carries a point mutation in Ser481 to Ala. A specific example for such mutant is provided by a mutant having the amino acid sequence as denoted by SEQ ID NO. 1.

According to another embodiment, the therapeutically effective amount of mutated tPA molecule, and any functional fragments or peptides administered by the method of the invention may range from about 1 µg/kg to about 100 mg/Kg body weight, more specifically, about 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2 mg/kg, 3 mg/kg, 4 mg/kg, 5 mg/kg, 6 mg/kg, 7 mg/kg, 8 mg/kg, 9 mg/kg and 10 mg/kg. A specific embodiment is an effective amount of about 1 mg/kg. Another specific embodiment is an effective amount of about 5 mg per Kg of body weight. This effective amount is preferably comprised within a dosage unit form.

It should be noted that for the methods of treatment and prevention provided in the present invention, said therapeutic effective amount, or dosage, is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the composition of the invention in bodily fluids or tissues. Following successful treatment, it may be desirable to have the patient undergo maintenance therapy to prevent the recurrence of the disease state, wherein the composition of the invention is administered in maintenance doses, once or more daily.

It should also be appreciated that the prevention or reduction of the risk of developing a neurodegenerative disorder is also encompassed within the scope of the invention. Such method may comprise the administration of a prophylactically effective amount of the composition of the invention or of the active ingredients comprised within such composition, to a person at risk of developing a disease.

The term "prophylactically effective amount" is intended to mean that amount of a pharmaceutical combined composition that will prevent or reduce the risk of occurrence of the biological or medical event that is sought to be prevented in a tissue, a system, animal or human by a researcher, veterinarian, medical doctor or other clinician.

A further aspect of the invention relates to the use of a therapeutically effective amount of a tPA mutated molecule devoid of total or partial serine protease activity, or any functional fragments or peptides thereof, in the preparation of a pharmaceutical composition for the treatment, amelioration or prophylaxis of a pathologic condition involving neurological injury.

The invention further provides a tPA mutated molecule devoid of serine protease activity, or any functional fragments or peptides thereof, for treating a pathologic condition involving neurological injury or an ischemic disease or condition.

According to one embodiment, tPA mutated molecule devoid of serine protease activity, or any functional fragments or peptides thereof is used for treating and preventing pathologic condition involving neurological injury or damage. Such pathologic condition may be any one of acute or traumatic brain injury, stroke, brain anoxia, prenatal brain damage, global and focal ischemic and hemorrhagic stroke, head trauma, spinal cord injury, neurosurgery intervention hypoxia-induced nerve cell damage such as in cardiac arrest or neonatal distress, epilepsy, anxiety, and a neurodegenerative disorder.

In another embodiment, the use of a tPA mutated molecule devoid of serine protease activity, or any functional fragments or peptides thereof according to the invention may be suitable for a subject suffering of a neurodegenerative disorder such as for example Alzheimer's disease, Parkinson's disease, ALS (Amyotrophic Lateral Sclerosis), Huntington's disease, taupathies such as Pick's disease, fronto temporal dementia, cortico-basal degeneration and progressive supranuclear palsy and Spongiform encephalopathies such as Scrapie, mad cow disease and Bovine spongiform encephalopathy, Creutzfeldt-Jakob disease, Fatal Familial Insomnia, Gerstmann-Straussler-Scheinker syndrome and Kuru.

In yet another embodiment, the tPA mutated molecule devoid of serine protease activity, or any functional fragments or peptides thereof used by the invention should be in therapeutically effective amount, which preferably being in a dosage unit form comprising from about 1 µg to about 100 mg per Kg of body weight, more specifically about 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 200 µg/kg, 300 µg/kg, 400 µg/kg, 500 µg/kg, 600 µg/kg, 700 µg/kg, 800 µg/kg, 900 µg/kg, 1000 µg/kg, 2 mg/kg, 3 mg/kg, 4 mg/kg, 5 mg/kg, 6 mg/kg, 7 mg/kg, 8 mg/kg, 9 mg/kg and 10 mg/kg. A specific embodiment is an effective amount of about 1 mg/kg. Another specific embodiment is an effective amount of about 5 mg per Kg of body weight.

According to a preferred embodiment, the mutated tPA molecule used by the invention carries at least one point mutation located at any position of residues Ser481, His325, Asp374, Asp475 Ser500 and Gly502 and any combinations thereof. According to another embodiment, the mutated molecule carries a point mutation in Ser481 to Ala. A specific example for such mutant is provided by a mutant having the amino acid sequence as denoted by SEQ ID NO. 1.

According to a specific embodiment, the tPA mutated molecule used is as described by the invention.

In another specific embodiment of this aspect, the tPA mutated molecule or any functional fragments or peptides thereof used by the invention is capable of increasing permeability of the BBB.

Therefore, the invention further provides the use of a tPA mutated molecule devoid of serine protease activity, or any functional fragments or peptides thereof, in the preparation of a composition for enhancing clearance of neurotoxic agents, wherein said mutated molecule is capable of increasing permeability of the BBB and thereby inhibit, ameliorate or prevent the accumulation of neurotoxic agents.

In another specific embodiment of this aspect, the tPA mutated molecule or any functional fragments or peptides thereof used by the invention is capable of inhibiting tPA activation of NMDA-R.

The invention therefore further provides the use of a tPA mutated molecule devoid of serine protease activity, or any functional fragments or peptides thereof, in the preparation of a composition for inhibiting tPA activation of NMDA-R, wherein said mutated molecule is capable of inhibiting tPA activation of NMDA-R and thereby inhibit, ameliorate or prevent NMDA-R mediated disorders.

According to a specific embodiment of this aspect the tPA mutated molecule used is as described by the invention.

The invention further provides a tPA mutated molecule devoid of serine protease activity, or any functional fragments or peptides thereof, for treating a pathologic condition involving neurological injury or an ischemic disease or condition.

Disclosed herein is a novel therapeutically effective formulation involving a combination of at least one tPA mutated molecule and at least one glutamate scavenger selected from the group consisting of glutamate-pyruvate transaminase (GPT), glutamate-oxaloacetate transaminase (GOT), Insulin, Glucagon and any combinations thereof, specifically, at least one of GPT and GOT.

As shown by FIG. 7, a combination of the tPA mutated molecule of the invention with the glutamate scavenger compounds lead to a significant increase in the permeability of the BBB and thereby to a synergistic beneficial effect on the NSS of a subject suffering of a CHI. The present invention therefore particularly relates to safe, non-interfering, additive and synergistic combinations of tPA mutant and glutamate scavenger molecules, or of pharmaceutically acceptable salts thereof, whereby those additive and synergistic combinations are useful in treating subjects suffering from a pathologic disorder such as stroke and any neurological injury. The non-interfering, synergistic and additive compositions of the invention may also be used for the treatment of Subjects presenting with symptoms or signs of such disorders.

By synergic combination is meant that the effect of both mutated tPA molecules of the invention and glutamate scavenger drugs is greater than the sum of the therapeutic effects of administration of any of these compounds separately, as a sole treatment.

The combination of Glutamate scavenger agent and the tPA mutated molecule of the invention may be prepare at a quantitative ratio of between 1:0.1 to 1:1000. It should be appreciated that any quantitative ratio may be used, for example, 1:1, 1:2, 1:3, 1:4, 1:5, 1:6, 1:7, 1:8, 1:9, 1:10, 1:20, 1:30, 1:40, 1:50, 1:100, 1:150, 1:200, 1:250, 1:300, 1:350, 1:400, 1:450, 1:500 and any possible combination thereof.

According to one embodiment, the combined composition of the invention is intended for elevating the permeability of the BBB or reducing the integrity of the BBB, in a subject in need thereof. The BBB permeability may increase by at least 5%, at least 10%, at least 15%, at least 20%, at least 25%, at least 30%, 35%, at least 40%, 45%, at least 50%, 55%, 60%, 65%, 70%, 75%, 80%, 85%, 90% or even at least 95% or 99% as compared to the level prior to treatment.

The invention therefore further provides a pharmaceutical unit dosage form comprising at least one tPA mutated molecule devoid of serine protease activity or any functional fragments or peptides thereof or any combination or mixture thereof, or a pharmaceutically acceptable derivative thereof, and optionally at least one glutamate scavenger selected from the group consisting of glutamate-pyruvate transaminase (GPT), glutamate-oxaloacetate transaminase (GOT), Insulin, Glucagon and any combinations thereof, specifically, at least one of GPT and GOT or any combination thereof, and a pharmaceutically acceptable carrier or diluent.

The combined compounds of the present invention are generally administered in the form of a pharmaceutical composition comprising all combined compounds of this invention together with a pharmaceutically acceptable carrier or diluent. Thus, the compounds used by this invention can be administered either individually in a kit or together in any conventional parenteral, oral or transdermal dosage form.

More particularly, since the present invention relates to the treatment of diseases and conditions with a combination of active ingredients which may be administered separately, the invention also relates as a further aspect, to combining separate Pharmaceutical compositions in kit form. The kit includes two separate pharmaceutical compositions: at least one tPA mutated molecule, any fragments thereof or any combination or mixture thereof, optionally, in a first dosage unit form, and at least one glutamate scavenger agent any combinations thereof or a pharmaceutically acceptable salt thereof, optionally, in a second dosage unit form. The kit includes container means for containing both separate compositions; such as a divided bottle or a divided foil packet however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

According to one embodiment the kit of the invention is intended for achieving a therapeutic effect in a subject suffering from a pathologic condition involving neurological injury or an ischemic disease or condition for example, stroke, acute or traumatic brain injury and a neurodegenerative disorder.

Achieving a therapeutic effect is meant for example, slowing the progression of neurological injury condition. According to one embodiment, such therapeutic effect may be reflected by the reduction of the NSS in the treated subject.

Still further, the invention provides a method of treatment of a pathologic disorder comprising the step of administering to a subject in need thereof a therapeutically effective amount of a first and a second unit dosage forms comprised in the kit according to the invention.

It should be appreciated that both components of the kit, the tPA mutated molecule of the invention in the first dosage form and the different glutamate scavenger compounds in the second dosage form may be administered simultaneously.

Alternatively, said first compound or dosage form and said second compound or dosage form are administered sequentially in either order.

The invention further provides a method for preventing or reducing the risk of neuronal injury disease comprising the administration of a prophylactically effective amount of a first and a second unit dosage forms comprised in the kit of the invention, to a person at risk of developing ischemic disease or condition.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Animals

Eight to twelve weeks old C57 mice obtained from Harlan, Israel.

Mice were administered standard laboratory chow and water ad libitum, and kept in controlled temperature and light conditions. Animal experiments were carried out according to the guidelines of the Hebrew University-Institutional Committee for Care and Use of Laboratory Animals, and with the committee's approval.

Construction of tPA Mutant:

The cDNA fragment encoding mature human tPA sequence was amplified by PCR with the primers of SEQ ID NO. 4 and 5, designed to introduce the 5'-flanking Bgl II and 3'-flanking Xho I restriction sites, respectively. The amplified fragment was digested with Bgl II and Xho I restriction enzymes, and cloned into corresponding sites of the pMT/BiP/V5-HisA plasmid (Invitrogen).

S481A mutation in tPA sequence was obtained by PCR with the pair of anti-parallel primers of SEQ ID NO. 6 and 7, using the QuickChange Mutagenesis kit (Stratagen). Both sequences for the wild type and mutant constructs were thoroughly sequenced to confirm lack of PCR-introduced errors. Both the recombinant wt and S481A mutant protein sequences contain 2 extra amino acids, RS-, at the N-terminus as the result of introduction of Bgl II cloning site into the original cDNA sequence encoding human tPA.

Expression and Purification of tPA Mutant

Recombinant human tPA and its catalytically inactive counterpart S481A tPA were expressed in S2 *Drosophila* Expression System (Invitrogen). The proteins were affinity purified using American Diagnostica PAM-1 MAb to tPA (Product #371, currently discontinued) coupled to CNBr-activated Sepharose 4 Fast Flow (Amersham Biosciences). The proteins were eluted with 0.1M glycine-HCl buffer, pH2.8 containing 0.2M Arg. The eluate was collected into PBS/0.2M Arg containing 80 microliters of 1M Tris-HCl, pH 8.0 per each ml of the eluate.

Protein concentration/buffer change for PBS/0.2M Arg was performed on Amicon 30K filtering device. 3-5 micrograms of the purified proteins appears on SDS-PAGE as a single band of expected size with no contaminants. The proteins were stored at $-70°$ C. or lyophilized CHI Experimental Model:

Head trauma was induced by using a modified weight-drop device, as previously described [Chen, Y., Constantini, S., Trembovler, V., Weinstock, M. & Shohami, E. (1996) *J. Neurotrauma* 13, 557-568].

Briefly, after induction of ether anesthesia, a midline longitudinal incision was made, the skin was retracted and the skull was exposed. The left anterior frontal area was identified and a Teflon tipped cone (2-mm diameter) was placed 1 mm lateral to the midline, in the midcoronal plane. The head was held in place manually and a 75-g weight was dropped on the cone from a height of 18 cm, resulting in focal injury to the left hemisphere. After trauma, the mice received supporting oxygenation with 95% $O_2$ for no longer than 2 min and were then returned to their cages. In sham controls only anesthesia and skin incision were carried out.

Neurobehavioral Evaluation

The neurological severity score (NSS) is a 10-point scale that assesses the functional neurological status of mice based on the presence of various reflexes and the ability to perform motor and behavioral tasks such as beam walking, beam balance, and spontaneous locomotion [Beni-Adani, L. J.

Pharmacol. Exp. Ther. 296:57-63 (2001)]. Animals were awarded one point for failure to perform one item, so that scores can range from zero (healthy uninjured animals) to a maximum of 10, indicating severe neurological dysfunction, with failure to perform all tasks. The NSS obtained 1 h after trauma reflects the initial severity of injury and is inversely correlated with the neurological outcome. Animals were evaluated 5 h after CHI, and every two to three days until 20 days later. Each animal was assessed by an observer who was blinded to the treatment.

Evaluation of Lactate and Glutamate Concentration in the Brain

CSF samples were taken from the cisterna magna in anaesthetized mice, using a microcapillary as described by others. Samples were immediately frozen at $-70°$ C. until analysis by high-performance liquid chromatography (HPLC). Glutamate and lactate were derivatized using ortho-phthaldialdehyde/b-mercaptoethanol and the samples were injected onto the column. Peaks were detected using a fluorescence detector.

Statistical Analysis:

Differences were analyzed using the t-test and the level of significance was corrected using a post-hoc analysis with the Bonferroni test. Statistical significance was set at $P<0.05$.

Example 1

Attenuation of Neurological Impairment after CHI by a tPA Mutant tPA has been reported to signal within the central nervous system by activating NMDA-R, a receptor for glutamine, implicated in neurotoxicity and exictotoxic neuronal cell death, through the cleavage of the NR-1 subunit of NMDA-R. The inventors therefore examined the effect of inhibiting tPA activation of NMDA-R on acute brain trauma, using a tPA mutated molecule devoid of serine protease catalytic activity. Therefore, a tPA mutant carrying a single replacement of Ser 481 to Ala has been synthesized. This mutant lacks any PA catalytic activity (data not shown) but is still able to mimic some of the extra catalytic activities of tPA, for example, opening of the Blood Brain Barrier. Experimental closed head injury (CHI) have been used to examine the effect of mutant tPA on post TBI response, therefore, groups of 8-9 animals were injected with mutant tPA, WT-tPA (100 μg/mice) in saline or saline alone intraperitoneally (i.p.) two hours after the head trauma. The effect of administering mutant tPA compositions was assessed using neurobehavioral evaluation based on the determination of a neurological severity score (NSS).

As shown in FIG. 1, mutant tPA administration improved the neurological status of CHI mice. The NSS of animals treated with mutant tPA was significantly lower than that of control animals (0.43 in mutant tPA treated mice as compared to 3.25 in saline treated control mice), indicating a neuroprotective effect induced by the mutant tPA.

In contrast to this neuroprotective effect, injection of WT tPA exerted a deleterious effect upon CHI mice, as shown by FIG. 2. The NSS of mice in this group at day 20 following CHI was significantly higher than that of control mice treated with saline or with mutant tPA. In this experiment, injection of tPA-S481A (mtPA) two hours post-CHI significantly improved initial (not shown) and long-term (FIG. 2) neurological outcome.

After the last NSS evaluation (day 20 post CHI) the brains were then extracted and sectioned coronally into 1-mm segments. The sections were photographed and the area of each section was determined using the NIH computer image analysis program. Any missing area was estimated by overlaying the affected section with images from the contralateral side from the same animal. The volume of the missing portion of the brain was defined as the sum of the missing areas in all sections multiplied by their thickness expressed in cubic pixels. Lesion size was significantly ($p<0.005$) smaller in animals that had been given tPA-$S^{481}$A compared to control animals (41525±10987 pixels vs. 64309±21345 pixels), whereas WT-tPA increased the lesion size significantly ($p<0.005$) compared to controls (167289±31456 pixels). Taken together, the data collected indicate that the tPA-S481A has a neuroprotective effect.

Without being bound to any theory, these results may indicate that the mutant tPA lacking the catalytic activity but still capable of mimicking some of the extra catalytic activities of tPA, competes with, endogenous TBI induced tPA. This competitive effect helps in ameliorating tPA induced neurotoxicity.

Example 2

Permeabilization of the Blood Brain Barrier (BBB) by a tPA Mutant

Loss of BBB integrity after TBI or stroke is generally assumed to have a deleterious effect on brain function. This stems from the accumulation of glutamate leading to secondary head injury. BBB integrity is compromised further by therapeutic concentrations of tPA. The effect of tPA on the BBB is mediated through the LDL receptor-related protein LRP and requires its catalytic activity.

To determine the effect of injection of tPA-$S^{481}$A on BBB function, anesthetized mice were injected i.p. with 25 μl of saline or saline containing tPA or tPA mutant (tPA-$Ser^{481}$Ala) (1 mg/kg each), followed by the intravenous injection of 2% Evans blue in saline. Evans blue was quantified by absorbance at 620 nm. As clearly shown by FIG. 3, a single i.p. injection of the mutated tPA molecule of the invention, tPA-$S^{481}$A, increased BBB permeability similar to the results of wild type, WT-tPA.

Plasminogen activator inhibitor-1 (PAI-1) is recognized as the inhibitor of tPA. The inventors have developed two PAI-1 derived peptides; the first as denoted by SEQ ID NO. 3 is 6 amino acids (aa) in length, and the second, as denoted by SEQ ID NO. 8 is an 18 amino acid peptide. The inventors used these two PAI-1 derived peptides to further access whether they are capable of inhibiting the tPA-mediated BBB opening. For this purpose, groups of 8-9 anesthetized mice were injected i.p. With 25 μl of saline or saline containing either WT-tPA or tPA-$Ser^{481}$Ala (1 mg/kg each) alone or together with the PAI-1 derived 18-aa (SEQ ID NO. 8) or 6-aa (SEQ ID NO. 3) peptides (1 mg/kg each). Mice were given an i.v. injection of 2% Evans blue (EB) in saline 10 min after the i.p. injection of the tPAs with or without the peptides. One hour after injection of the dye, organs were cleared of blood by transcardiac perfusion. The brains were removed, photographed, weighed, homogenized in N,N-dimethylformamide and centrifuged. Extruded dye was quantified by absorbance at 620 nm. Data are expressed in FIG. 4A as absorbance per gram of tissue. The results presented in FIG. 4A are in line with the findings of FIG. 3, clearly demonstrating that a single i.p. injection of tPA-$S^{481}$A increases BBB permeability to the same extent as WT-tPA. Interestingly, while the EEIIMD (SEQ ID NO. 3) failed to decrease the recombinant tPA-induced BBB permeability, the 18-aa PAI-1 derived peptide (SEQ ID NO. 8) injection resulted in an almost total inhibition of the rtPA-mediated BBB opening.

FIG. 4B shows a representative image of the distribution of EB injected i.v. 10 min after CHI.

Prolonged Duration of Blood Brain Barrier (BBB) Permeability after CHI by the tPA Mutant To examine the effect of tPA-S481A (mtPA) on BBB permeability after opening due to CHI, the tPA mutant was injected to 8-9 mice i.p. 1, 2 or 3 hours after CHI. Mice undergoing CHI alone served as controls for the indication of normal BBB behavior after head trauma. In both groups, the extravasation of EB was measured one hour after injection of the dye. The results presented in FIG. 5 show that BBB integrity is lost 10 min after CHI, and this integrity is almost fully restored to the level observed prior to the trauma within 3 hours. In contrast, exposure to mtPA within 2-3 hours of CHI markedly extended the duration of increased BBB permeability.

Example 3

Reducing Glutamate in the Brain is Neuroprotective

The inventors next hypothesize that one mechanism by which mtPA increases BBB permeability, while providing neuroprotection, is by promoting the elimination of neurotoxic amino acids from the brain. It was previously shown that decreasing blood glutamate levels enhances the transport of radiolabel glutamate injected into the brain from the CNS into the peripheral circulation. [Zotnik, A. et al. *Exp. Neurology* 203:213-220 (2007)]. Therefore, the inventors examined the effect of the tPA mutated molecule in facilitating the clearance of neurotoxic agents during head injury, using the experimental closed head trauma (CHI) model.

Therefore, groups of 8-9 animals were injected with mutant tPA, (100 μg/mice) in saline or saline alone intraperitoneally (i.p.) two hours after the head trauma and, the concentration of lactate and glutamate in the CSF have been measured.

As shown in FIG. 6, the inactive mutant of the invention, tPA-S481A, clearly alleviates the accumulation of lactate (FIG. 6A) and glutamate (FIG. 6B) post-TBI damage, probably by enabling the permeabilization of the BBB to the same extent as the WT tPA (as shown by FIG. 5).

Plasma glutamate-pyruvate transaminase (GPT) and glutamate-oxaloacetate transaminase (GOT), transforms glutamate into 2-ketoglutarate in the presence of their respective co-substrates, pyruvate and oxaloacetate. In this model, i.v. administration of oxaloacetate (0.005 mmol/100 g) combined with recombinant GOT (0.14 nmol/100 g) decreased blood glutamate by 40% in rats and provided extensive neuroprotection and enhanced recovery post-CHI [Gottlieb, et al., *J. Neurochem.* 87:119-126 (2003)]. Therefore, the inventors tested whether the neuroprotective effect of the blood glutamate scavenger, which promotes clearance of glutamate from the brain after trauma, would be enhanced by opening the BBB with mtPA. The scavenger comprising Oxaloacetate and recombinant GOT was given i.v. 10 min (BBB is permeable) or 2 hours (BBB permeability has been restored) after CHI mutated tPA was given two hours after CHI alone or with the scavenger, by which time BBB integrity has recovered. The NSS was assessed on day 20.

As clearly shown in FIG. 7, the glutamate scavenger provided significant neuroprotection when it was given 10 minutes after the CHI, a finding which is in line with previous reports [Gottlieb (2003) ibid.]. In contrast, injection of the scavenger two hours after induction of the head injury did not provide any protective effect. The beneficial effect of the glutamate scavenger shown in FIG. 7 parallels the natural loss and restoration of BBB integrity as demonstrated in FIG. 5. This outcome is consistent with the notion that the effectiveness of the scavenger depends on the BBB opening required for glutamate to efflux from the brain into the blood, among other potential mechanisms. Further, FIG. 7 clearly demonstrates a synergy of the beneficial effect of the glutamate scavenger and mutated tPA molecule of the invention, resulting in a significant improvement of the neurological functions. The synergistic effect correlated with the ability of the mutated molecule of the invention, tPA-S$^{481}$A, to open the BBB. Taken together, the data presented in FIG. 7 support the concept that the reopening of the BBB by the mutated tPA molecule of the invention permitted the efflux of glutamate from the brain to the circulation. Furthermore, the data indicate that BBB permeability is essential for the scavenger to be effective.

Without being bound to any theory, these results may indicate that the mutant tPA lacking the catalytic activity is still capable of mimicking some of the extra catalytic activities of tPA, specifically the opening or increasing the permeability of the BBB and that it is this opening that facilitates the clearance of neurotoxic agents such as glutamate and lactate from the brain and the CSF further promoting the salutary effect of the tPA mutant on neurological outcome.

TABLE 1

| SEQ ID NO. | sequence listing: Sequence Description |
|---|---|
| 1 | Mutant tPA-Ser481Ala |
| 2 | WT tPA |
| 3 | The 6 aa PAI-1 derived peptide |
| 4 | Primer htPA-Bgl II |
| 5 | Primer htPA-Xho I |
| 6 | Anti-parallel primers for introduction of the Ser481Ala mutation |
| 7 | Anti-parallel primers for introduction of the Ser481Ala mutation |
| 8 | The 18 aa PAI-1 derived peptide |

The invention claimed is:

1. A method for the treatment of acute or traumatic brain injury or cerebral ischemia, comprising administering to a subject suffering from said condition a therapeutically effective amount of a protein comprising a tPA mutated molecule devoid of serine protease activity, or a composition comprising the same, wherein said tPA mutated molecule has at least 522 amino acids that are identical to SEQ ID NO: 1 and has an alanine residue at the position corresponding to Ala$^{483}$ of SEQ ID NO: 1.

2. The method according to claim 1, wherein said cerebral ischemia is stroke.

3. The method according to claim 1, wherein said pathologic condition is acute or traumatic brain injury.

4. The method according to claim 1, wherein said at least one tPA mutated molecule or any compositions comprising the same increases the permeability of the BBB (blood-brain-barrier) in said subject.

5. The method according to claim 1, wherein said at least one tPA mutant or any composition comprising the same leads to reduction of the NSS (neurological severity score) in said subject.

6. The method according to claim 3, wherein said pathologic condition involving neurological injury is traumatic brain injury (TBI).

7. The method of claim 1 wherein the tPA mutated molecule is lacking residues Arg$^1$ and Ser$^2$ of SEQ ID NO: 1.

8. The method according to claim 1, wherein the tPA mutated molecule consists of the amino acid sequence of SEQ ID NO: 1.

9. The method according to claim 1, wherein the tPA mutated molecule is as set forth by residues 3-532 of SEQ ID NO: 1.

10. A method for the treatment of acute or traumatic brain injury or cerebral ischemia, comprising administering to a subject suffering from said condition a therapeutically effective amount of a protein comprising a tPA mutated molecule devoid of serine protease activity and an additional therapeutic agent, or a composition comprising the same, wherein said tPA mutated molecule has at least 522 amino acids that are identical to SEQ ID NO: 1 and has an alanine residue at the position corresponding to Ala$^{483}$ of SEQ ID NO: 1.

11. The method according to claim 10, wherein said additional therapeutic agent is a glutamate scavenger selected from the group consisting of glutamate-oxaloacetate transaminase (GOT), oxaloacetate, and the combination thereof.

12. The method according to claim 11, wherein said glutamate scavenger is glutamate-oxaloacetate transaminase (GOT).

13. The method according to claim 10, wherein said pathologic condition is acute or traumatic brain injury.

14. The method according to claim 13, wherein said pathologic condition is traumatic brain injury (TBI).

15. The method according to claim 10, wherein said cerebral ischemia is stroke.

16. The method according to claim 10, wherein the at least one tPA mutated molecule or any compositions comprising the same and an additional therapeutic agent, increases the permeability of the BBB (blood-brain-barrier) in said subject.

17. The method according to claim 10, wherein said at least one tPA mutant or any composition comprising the same and an additional therapeutic agent, leads to reduction of the NSS (neurological severity score) in said subject.

18. The method according to claim 10, wherein the tPA mutated molecule is lacking residues Arg$^1$ and Ser$^2$ of SEQ ID NO: 1.

19. The method according to claim 10, wherein the tPA mutated molecule consists of the amino acid sequence of SEQ ID NO. 1.

20. The method according to claim 10, wherein the tPA mutated molecule is as set forth by residues 3-532 of SEQ ID NO: 1.

* * * * *

UNITED STATES PATENT AND TRADEMARK OFFICE
CERTIFICATE OF CORRECTION

PATENT NO. : 9,072,737 B2
APPLICATION NO. : 12/922551
DATED : July 7, 2015
INVENTOR(S) : Abd Higazi et al.

Page 1 of 1

It is certified that error appears in the above-identified patent and that said Letters Patent is hereby corrected as shown below:

In the Claims

Claim 7, column 35, line 61, delete "residues Arg' and Ser$^{2}$" and insert -- residues Arg$^{1}$ and Ser$^{2}$ --.

Claim 18, column 36, line 66, delete "residues Arg' and Ser$^{2}$" and insert -- residues Arg$^{1}$ and Ser$^{2}$ --.

Signed and Sealed this
Third Day of May, 2016

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 532
<212> TYPE: PRT
<213> ORGANISM: Homo sapiens

<400> SEQUENCE: 1

Arg Ser Gly Ala Arg Ser Tyr Gln Val Ile Cys Arg Asp Glu Lys Thr
1               5                   10                  15
```

```
Gln Met Ile Tyr Gln Gln His Gln Ser Trp Leu Arg Pro Val Leu Arg
             20                  25                  30

Ser Asn Arg Val Glu Tyr Cys Trp Cys Asn Ser Gly Arg Ala Gln Cys
             35                  40                  45

His Ser Val Pro Val Lys Ser Cys Ser Glu Pro Arg Cys Phe Asn Gly
 50                  55                  60

Gly Thr Cys Gln Gln Ala Leu Tyr Phe Ser Asp Phe Val Cys Gln Cys
 65                  70                  75                  80

Pro Glu Gly Phe Ala Gly Lys Cys Cys Glu Ile Asp Thr Arg Ala Thr
                 85                  90                  95

Cys Tyr Glu Asp Gln Gly Ile Ser Tyr Arg Gly Thr Trp Ser Thr Ala
                100                 105                 110

Glu Ser Gly Ala Glu Cys Thr Asn Trp Asn Ser Ser Ala Leu Ala Gln
                115                 120                 125

Lys Pro Tyr Ser Gly Arg Arg Pro Asp Ala Ile Arg Leu Gly Leu Gly
            130                 135                 140

Asn His Asn Tyr Cys Arg Asn Pro Asp Arg Asp Ser Lys Pro Trp Cys
145                 150                 155                 160

Tyr Val Phe Lys Ala Gly Lys Tyr Ser Ser Glu Phe Cys Ser Thr Pro
                165                 170                 175

Ala Cys Ser Glu Gly Asn Ser Asp Cys Tyr Phe Gly Asn Gly Ser Ala
                180                 185                 190

Tyr Arg Gly Thr His Ser Leu Thr Glu Ser Gly Ala Ser Cys Leu Pro
            195                 200                 205

Trp Asn Ser Met Ile Leu Ile Gly Lys Val Tyr Thr Ala Gln Asn Pro
            210                 215                 220

Ser Ala Gln Ala Leu Gly Leu Gly Lys His Asn Tyr Cys Arg Asn Pro
225                 230                 235                 240

Asp Gly Asp Ala Lys Pro Trp Cys His Val Leu Lys Asn Arg Arg Leu
                245                 250                 255

Thr Trp Glu Tyr Cys Asp Val Pro Ser Cys Ser Thr Cys Gly Leu Arg
            260                 265                 270

Gln Tyr Ser Gln Pro Gln Phe Arg Ile Lys Gly Gly Leu Phe Ala Asp
            275                 280                 285

Ile Ala Ser His Pro Trp Gln Ala Ala Ile Phe Ala Lys His Arg Arg
290                 295                 300

Ser Pro Gly Glu Arg Phe Leu Cys Gly Gly Ile Leu Ile Ser Ser Cys
305                 310                 315                 320

Trp Ile Leu Ser Ala Ala His Cys Phe Gln Glu Arg Phe Pro Pro His
                325                 330                 335

His Leu Thr Val Ile Leu Gly Arg Thr Tyr Arg Val Val Pro Gly Glu
            340                 345                 350

Glu Glu Gln Lys Phe Glu Val Glu Lys Tyr Ile Val His Lys Glu Phe
            355                 360                 365

Asp Asp Asp Thr Tyr Asp Asn Asp Ile Ala Leu Leu Gln Leu Lys Ser
            370                 375                 380

Asp Ser Ser Arg Cys Ala Gln Glu Ser Ser Val Val Arg Thr Val Cys
385                 390                 395                 400

Leu Pro Pro Ala Asp Leu Gln Leu Pro Asp Trp Thr Glu Cys Glu Leu
                405                 410                 415

Ser Gly Tyr Gly Lys His Glu Ala Leu Ser Pro Phe Tyr Ser Glu Arg
            420                 425                 430
```

```
Leu Lys Glu Ala His Val Arg Leu Tyr Pro Ser Ser Arg Cys Thr Ser
        435                 440                 445

Gln His Leu Leu Asn Arg Thr Val Thr Asp Asn Met Leu Cys Ala Gly
        450                 455                 460

Asp Thr Arg Ser Gly Gly Pro Gln Ala Asn Leu His Asp Ala Cys Gln
465                 470                 475                 480

Gly Asp Ala Gly Gly Pro Leu Val Cys Leu Asn Asp Gly Arg Met Thr
                    485                 490                 495

Leu Val Gly Ile Ile Ser Trp Gly Leu Gly Cys Gly Gln Lys Asp Val
                500                 505                 510

Pro Gly Val Tyr Thr Lys Val Thr Asn Tyr Leu Asp Trp Ile Arg Asp
        515                 520                 525

Asn Met Arg Pro
    530

<210> SEQ ID NO 2
<211> LENGTH: 530
<212> TYPE: PRT
<213> ORGANISM: Homo sapiens

<400> SEQUENCE: 2

Gly Ala Arg Ser Tyr Gln Val Ile Cys Arg Asp Glu Lys Thr Gln Met
1               5                   10                  15

Ile Tyr Gln Gln His Gln Ser Trp Leu Arg Pro Val Leu Arg Ser Asn
            20                  25                  30

Arg Val Glu Tyr Cys Trp Cys Asn Ser Gly Arg Ala Gln Cys His Ser
        35                  40                  45

Val Pro Val Lys Ser Cys Ser Glu Pro Arg Cys Phe Asn Gly Gly Thr
50                  55                  60

Cys Gln Gln Ala Leu Tyr Phe Ser Asp Phe Val Cys Gln Cys Pro Glu
65                  70                  75                  80

Gly Phe Ala Gly Lys Cys Cys Glu Ile Asp Thr Arg Ala Thr Cys Tyr
                85                  90                  95

Glu Asp Gln Gly Ile Ser Tyr Arg Gly Thr Trp Ser Thr Ala Glu Ser
            100                 105                 110

Gly Ala Glu Cys Thr Asn Trp Asn Ser Ser Ala Leu Ala Gln Lys Pro
        115                 120                 125

Tyr Ser Gly Arg Arg Pro Asp Ala Ile Arg Leu Gly Leu Gly Asn His
        130                 135                 140

Asn Tyr Cys Arg Asn Pro Asp Arg Asp Ser Lys Pro Trp Cys Tyr Val
145                 150                 155                 160

Phe Lys Ala Gly Lys Tyr Ser Ser Glu Phe Cys Ser Thr Pro Ala Cys
                165                 170                 175

Ser Glu Gly Asn Ser Asp Cys Tyr Phe Gly Asn Gly Ser Ala Tyr Arg
            180                 185                 190

Gly Thr His Ser Leu Thr Glu Ser Gly Ala Ser Cys Leu Pro Trp Asn
        195                 200                 205

Ser Met Ile Leu Ile Gly Lys Val Tyr Thr Ala Gln Asn Pro Ser Ala
210                 215                 220

Gln Ala Leu Gly Leu Gly Lys His Asn Tyr Cys Arg Asn Pro Asp Gly
225                 230                 235                 240

Asp Ala Lys Pro Trp Cys His Val Leu Lys Asn Arg Arg Leu Thr Trp
                245                 250                 255

Glu Tyr Cys Asp Val Pro Ser Cys Ser Thr Cys Gly Leu Arg Gln Tyr
            260                 265                 270
```

Ser Gln Pro Gln Phe Arg Ile Lys Gly Gly Leu Phe Ala Asp Ile Ala
        275                 280                 285

Ser His Pro Trp Gln Ala Ala Ile Phe Ala Lys His Arg Arg Ser Pro
    290                 295                 300

Gly Glu Arg Phe Leu Cys Gly Gly Ile Leu Ile Ser Ser Cys Trp Ile
305                 310                 315                 320

Leu Ser Ala Ala His Cys Phe Gln Glu Arg Phe Pro Pro His His Leu
                325                 330                 335

Thr Val Ile Leu Gly Arg Thr Tyr Arg Val Val Pro Gly Glu Glu
        340                 345                 350

Gln Lys Phe Glu Val Glu Lys Tyr Ile Val His Lys Glu Phe Asp Asp
    355                 360                 365

Asp Thr Tyr Asp Asn Asp Ile Ala Leu Leu Gln Leu Lys Ser Asp Ser
370                 375                 380

Ser Arg Cys Ala Gln Glu Ser Ser Val Val Arg Thr Val Cys Leu Pro
385                 390                 395                 400

Pro Ala Asp Leu Gln Leu Pro Asp Trp Thr Glu Cys Glu Leu Ser Gly
                405                 410                 415

Tyr Gly Lys His Glu Ala Leu Ser Pro Phe Tyr Ser Gly Arg Leu Lys
        420                 425                 430

Glu Ala His Val Arg Leu Tyr Pro Ser Ser Arg Cys Thr Ser Gln His
    435                 440                 445

Leu Leu Asn Arg Thr Val Thr Asp Asn Met Leu Cys Ala Gly Asp Thr
450                 455                 460

Arg Ser Gly Gly Pro Gln Ala Asn Leu His Asp Ala Cys Gln Gly Asp
465                 470                 475                 480

Ser Gly Gly Pro Leu Val Cys Leu Asn Asp Gly Arg Met Thr Leu Val
                485                 490                 495

Gly Ile Ile Ser Trp Gly Leu Gly Cys Gly Gln Lys Asp Val Pro Gly
        500                 505                 510

Val Tyr Thr Lys Val Thr Asn Tyr Leu Asp Trp Ile Arg Asp Asn Met
    515                 520                 525

Arg Pro
530

<210> SEQ ID NO 3
<211> LENGTH: 6
<212> TYPE: PRT
<213> ORGANISM: Homo sapiens

<400> SEQUENCE: 3

Glu Glu Ile Ile Met Asp
1               5

<210> SEQ ID NO 4
<211> LENGTH: 39
<212> TYPE: DNA
<213> ORGANISM: Homo sapiens

<400> SEQUENCE: 4
gcccgattca gatctggagc ccgcagctac caagtgatc            39

<210> SEQ ID NO 5
<211> LENGTH: 37
<212> TYPE: DNA
<213> ORGANISM: Homo sapiens

```
<400> SEQUENCE: 5
ttttgaggac tcgagtgttc cttatcacgg tcgcatg                                37

<210> SEQ ID NO 6
<211> LENGTH: 33
<212> TYPE: DNA
<213> ORGANISM: Homo sapiens

<400> SEQUENCE: 6
gcctgccagg gcgatgccgg aggcccctg gtg                                     33

<210> SEQ ID NO 7
<211> LENGTH: 33
<212> TYPE: DNA
<213> ORGANISM: Homo sapiens

<400> SEQUENCE: 7
caccaggggg cctccggcat cgccctggca ggc                                    33

<210> SEQ ID NO 8
<211> LENGTH: 18
<212> TYPE: PRT
<213> ORGANISM: Homo sapiens

<400> SEQUENCE: 8

Arg Met Ala Pro Glu Glu Ile Ile Met Asp Arg Pro Phe Leu Phe Val
1               5                  10                  15

Val Arg
```